United States Patent [19]

Fukazawa et al.

[11] Patent Number: 5,405,843
[45] Date of Patent: Apr. 11, 1995

[54] QUINOLINE DERIVATIVES

[75] Inventors: Nobuyuki Fukazawa; Makoto Odate; Tsuneji Suzuki, all of Yokohama; Kengo Otsuka, Kamakura; Takashi Tsuruo; Wakao Sato, both of Tokyo, all of Japan

[73] Assignee: Mitsui Toatsu Chemicals, Incorporated, Tokyo, Japan

[21] Appl. No.: 123,842

[22] Filed: Sep. 9, 1993

Related U.S. Application Data

[63] Continuation of Ser. No. 871,050, Apr. 20, 1992, abandoned, which is a continuation of Ser. No. 417,780, Oct. 6, 1989, Pat. No. 5,112,817.

[30] Foreign Application Priority Data

Oct. 6, 1988 [JP] Japan .................. 63-250897
Jun. 22, 1989 [JP] Japan .................. 1-158315

[51] Int. Cl.⁶ .................. C07D 403/12; A61K 31/38
[52] U.S. Cl. .................. 514/183; 514/243; 514/248; 514/249; 514/253; 514/255; 514/258; 514/259; 514/260; 544/179; 544/183; 544/235; 544/284; 544/353; 544/354; 544/355; 544/356; 544/363

[58] Field of Search ............. 514/183, 243, 248, 249, 514/253, 255, 258, 259, 260; 544/179, 183, 235, 284, 353, 354, 355, 356, 363

[56] References Cited

U.S. PATENT DOCUMENTS

| | | | |
|---|---|---|---|
| 3,133,925 | 5/1964 | Cusic ..................... | 260/268 |
| 3,983,121 | 9/1976 | Murthi et al. ............. | 544/363 |
| 4,073,909 | 2/1978 | Troxler et al. ............ | 424/258 |
| 4,145,542 | 3/1979 | Nakagawa et al. .......... | 544/363 |
| 4,335,127 | 6/1982 | Vandenberk et al. ........ | 424/251 |
| 4,421,920 | 12/1983 | Baudouin et al. .......... | 546/163 |
| 4,749,703 | 6/1988 | Uno et al. ................ | 544/363 |
| 4,849,431 | 7/1989 | Sugimoto et al. .......... | 514/331 |
| 4,918,073 | 1/1987 | Rugger et al. ............ | 514/255 |
| 4,942,169 | 7/1990 | Sugimoto et al. .......... | 514/318 |
| 4,980,351 | 12/1990 | Barth .................... | 514/253 |
| 5,039,681 | 8/1991 | Sugimoto et al. .......... | 514/309 |
| 5,118,684 | 6/1992 | Sugimoto et al. .......... | 514/289 |

FOREIGN PATENT DOCUMENTS

| | | |
|---|---|---|
| 645414 | 7/1962 | Canada . |
| 0229623 | 7/1987 | European Pat. Off. . |
| 2567885 | 1/1986 | France . |
| 2163150 | 2/1986 | United Kingdom . |

OTHER PUBLICATIONS

Chemical Abstract, vol. 81, No. 17, 1974, pp. 526–527, No. 105445z Banerjee et al "Anticancer agents. III. Synthesis . . . Propanes".

*Primary Examiner*—Johann Richter
*Assistant Examiner*—Catherine S. Kilby Scalzo
*Attorney, Agent, or Firm*—Nixon & Vanderhye

[57] ABSTRACT

Heterocyclic compounds useful as anticancer drug potentiaters having a potentiating effect on the incorporation of anticancer drugs into cancer cells are disclosed, the compounds each synthesized by, for example, reacting a epoxy compound obtained by reacting a heterocyclic compound with an epihalogenohydrin, with an amine derivative.

17 Claims, No Drawings

QUINOLINE DERIVATIVES

This is a continuation of application Ser. No. 07/871,050, filed Apr. 20, 1992, now abandoned which in turn is a continuation of Ser. No. 07/417,780, filed Oct. 6, 1989, now U.S. Pat. No. 5,112,817.

BACKGROUND OF THE INVENTION

1. Field of the Invention

The present invention relates to novel compounds and anticancer drug potentiaters containing them as effective components.

2. Description of the Prior Art

Since the number of cancer patients is increasing year after year and cancer is the leading death cause today in many countries, cancer treatment is of great social interest.

Research and development regarding anticancer drugs for cancer treatment have been actively pursued and various anticancer drugs have been clinically used for therapeutic benefit. The effect of these agents steadily improves from year to year. However, in many cases, the agents do not necessarily completely control cancer growth and prolong the life of cancer patients. Furthermore, the use of multiple anticancer drugs in combination (multiple-drug treatment) have been tried in various clinical cases. However, likewise, the resulting effect is not entirely satisfactory cancer chemotherapy. Thus, development of novel therapeutic agents for the treatment of cancer from a fresh viewpoint is needed.

Development of more effective anticancer drugs or of means to deliver anticancer drugs more selectively to the target organs and tissues continues. Today, various research activities directed towards these goals are being conducted in many places throughout the world but only with increasing difficulty.

Another important aspect of cancer chemotherapy is potentiating the effects of chemotherapeutic agents. Development of potentinters to facilitate presently available anticancer drugs, in particular for multiple drug-resistant cancers which is a serious clinical problem in cancer chemotherapy, is considered to be extremely important in cancer therapy. The background of the clinical incidence of resistance of cancer to anticancer drugs is complex. Clinically, two aspects are generally considered. The first is where the resistance is attributed to individual cancer patients. The second is where the resistance is attributed o to cancer cells per se. Recently, as to the second aspect, the mechanism of tumor cell resistance has been elucidated at a molecular level and accordingly methods for therapy of this type of cancer resistance have been under investigation. Namely, a gene which is responsible for multi-drug-resistance has been recently isolated. It has been determined that this gene codes for a membrane protein, P-glycoprotein, and is expressed in multi-drug-resistant cells. It is suspected that the P-glycoprotein functions by promoting extracellular excretion of anticancer drugs and plays the central role in the mechanism of multiple-drug-resistance. Furthermore, it is suggested that the mechanism is partly common to that of the resistance to solid cancer which is by itself resistant to anticancer drugs.

Anticancer drugs primarily pass into the cell membrane to manifest their effect inside the cells; however, in drug-resistant cancer cells, anticancer drugs are discharged outside the cells due to the function of the P-glycoprotein, so that the drug concentration inside the cancer cells remains low. Consequently, the effect of the anticancer drugs is not exhibited to the fullest extent possible.

Accordingly, the present inventors consider that substances which can suppress the function of the P-glycoprotein so as to interfere with the outflow of anticancer drugs from cancer ceils have ability to potentate the effect of anticancer drugs and are particularly effective in overcoming drug resistance and thus make promising novel cancer chemotherapeutics.

In fact, Tsuruo et al. found that calcium antagonists such as verapamil prevent discharge of anticancer drugs from cancer cells and that, accordingly with the use of these 25 calcium antagonists in combination, the effect of anticancer drugs such as adriamycin and vincristine on drug-resistant cancer cells is reinforced in vitro and in vivo. However, in the case where these calcium antagonists are used clinically for cancer patients, side effects such as hypotonia and arhythmia occur, which creates another serious problem in cancer chemotherapy. Consequently, drugs which have a stronger potentiating activity for anticancer drugs against drug-resistant cancers and manifest fewer side effects are desired.

SUMHAIRY OF THE INVENTION

As a result of intensive investigations in view of above-mentioned problems, the present inventors found that certain compounds manifest strong activity to potentlate the effects of anticancer drugs when used against drug-resistant cancer and have low toxicity and fewer side effects, and thus completed the present invention.

The present invention relates compounds within the following general formula [I] and salts thereof (hereinafter referred to as the compounds according to the present invention) and to therapeutic compositions to potentiate the effect of anticancer drugs containing the compounds according to the present invention as active ingredients:

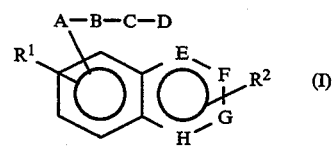

in which A represents an oxygen or sulfur atom or a methylene, amino or $-NR^3$ group. which is bound to any one of the available sites on the condensed ring, B represents $-g(CH_2)_n-$,

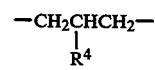

or $-CO(CH_2)_n-$, C represents

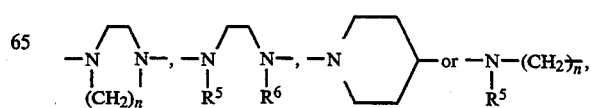

D represents 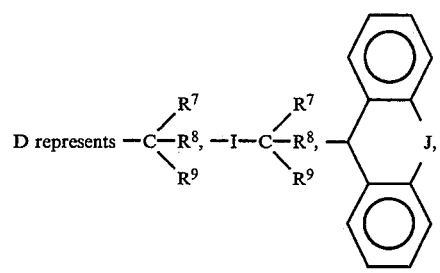

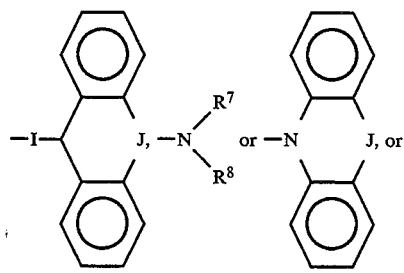

C and D together form 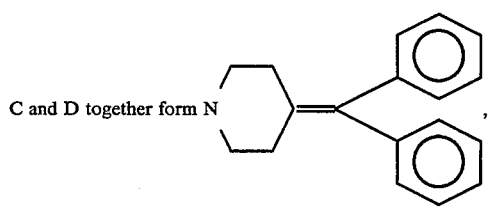

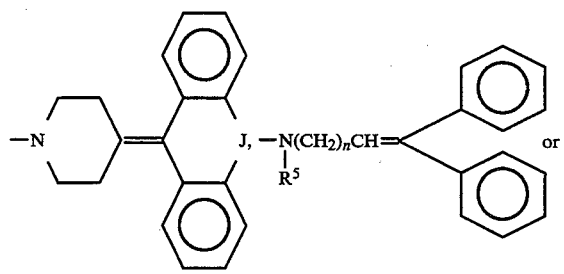

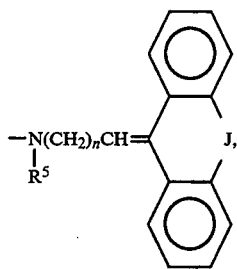

E, F, G and H each independently represent a carbon or nitrogen atom, provided at least one atom is nitrogen. $R^1$ and $R^2$ each independently represent a hydrogen or halogen atom, a lower alkyl, amino group, substituted amino group, a lower alkoxy, lower alkyl thio, lower alkylsulfonyl, trifluoromethyl, cyano, nitro, amide or hydroxy group, $R^1$ and $R^2$ may be substituted on any of the possible sites on the condensed ring and may be one on each of the two rings of which the condensed ring consists or two at the same time on one of the rings. $R^3$ represents a hydrogen atom or a lower alkyl or acyl group. $R^4$ represents a hydroxyl, lower alkylamino, lower alkoxyl or lower acyloxy group, $R^5$ and $R^6$ each independently represent a hydrogen atom or a lower alkyl or hydroxyalkyl group, $R^7$, $R^8$ and $R^9$ each independently represent a hydrogen atom or a hydroxy, phenyl, pyridyl or substituted phenyl group, I represents an oxygen atom, —$(CH_2)_{\overline{n}}$,

or a nitrogen atom, J represents —$(CH_2)_{\overline{m}}$, —CH=CH—, —$OCH_2$— or an oxygen atom, n represents an integral number in the range between 1 and 10, and m represents an integral number, 0, 1 or 2.

The compounds according to the present invention significantly suppress the outflow of anticancer drugs from cancer cells and, moreover, are characterized by their low toxicity and extremely low incidence of side effects to the patient such as hypotonia.

Accordingly, the compounds according to the present invention are effective to facilitate retenting anticancer drugs in cancer cells, which cells are less sensitive or resistant to anticancer drugs, and can thus provide new therapeutic means advance cancer chemotherapy.

DETAILED DESCRIPTION AND THE PREFERRED EMBODIMENTS

As used herein, the terms used above have the following meanings: a halogen atom means a fluorine atom, chlorine atom, bromine atom or iodine atom.

A lower alkyl group means a.methyl group, ethyl group, propyl group, butyl group, their positional isomers or the like.

A substituted amino group means a methylamino group, dimethylamino group, ethylamino group, diethylamino group, propylamino group, butylamino group or the like.

A lower alkoxy group means a methoxy group, ethoxy group, propoxy group, butoxy group or the like.

An amido group means a formamido group, acetamido group, benzamido group or the like.

An acyl group means a formyl group, acetyl group, propanoyl group, benzoyl group or the like.

An acyloxy group means a formyloxy group, acetoxy group or the like.

A hydroxyalkyl group means a 2-hydroxyethyl group, 2-hydroxypropyl group or 3-hydroxypropyl group or the like.

A substituted phenyl group means a halogenophenyl group, alkoxyphenyl group, aminophenyl group, alkylaminophenyl group, acylaminophenyl group, hydroxyphenyl group or the like which is substituted at the 2-, 3- or 4-position.

Examples of a partial structure of the general formula (I) represented by the formula

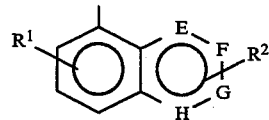

include 2-methylquinoline, 3-methylquinoline, 4-methylquinoline, 6-methylquinoline, 7-methylquinoline, 8-methylquinoline, 2-ethylquinoline, 3-ethylquinoline, 4-ethylquinoline, -ethylquinoline, 7-ethylquinoline, 8-ethylquinoline, 2,4-dimethylquinoline, 2,4-diethylquinoline, 7-nitroquinoline, 8-nitroquinoline, 2-methoxyquinoline, 3-methoxyquinoline, 4-methoxyquinoline, 6-methoxyquinoline, 7-methoxyquinoline, 8-methoxyquinoline, 2-chloroquinoline, 3-chloroquinoline, 4-chloroquinoline, 6-chloroquinoline, 7-chloroquinoline, 8-chloroquinoline, 2-trifluoromethylquinoline, -trifluoromethylquinoline, 4-trifluoromethylquinoline, -trifluoromethylquinoline, 7-trifluoromethylquinoline, -trifluoromethylquinoline, 2,4-bis(trifluoromethyl)quinoline, 2-fluoroquinoline, 3-fluoroquinoline, 4-fluoroquinoline, 6-fluoroquinoline, 7-fluoroquinoline, 8-fluoroquinoline, 2-bromoquinoline, 3-bromoquinoline, 4-bromoquinoline, 6-bromoquinoline, 7-bromoquinoline, 8-bromoquinoline, 2-iodoquinoline, 8-iodoquinoline, 2-propylquinoline, 3-propylquinoline, 2,4-dipropylquinoline, 8-propylquinoline 2-butylquinoline, 8-butylquinoline, 2,4-dibutylquinoline, 2-aminoquinoline, 7-aminoquinoline, 8-aminoquinoline, 2-methylaminoquinoline, 7-methylaminoquinoline, 8-methylaminoquinoline, 2-dimethylaminoquinoline, 7-dimethylamoinoquinoline, 8-dimethylaminoquinoline, 2-ethylaminoquinoline, 8-ethylaminoquinoline, 2-diethylaminoquinoline, 8-diethylaminoquinoline, 2-propylaminoquinoline, 8-propylaminoquinoline, 2-ethoxyquinoline, 7-ethoxyquinoline, 8-ethoxyquinoline, 2-propoxyquinoline, 7-propoxyquinoline, 2-butoxyquinoline, 8-butoxyquinoline, 2-cyanoquinoline, 2-formamidoquinoline, 2-acetamidoquinoline, 7-acetamidoquinoline, 8-acetamidequinoline, 3-hydroxyquinoline, 7-hydroxyquinoline, 8-hydroxyquinoline, isoquinoline, quinoxaline, quinazoline and cinnoline.

Examples of A, which is a partial structure of the general formula (I), include an oxygen atom —O—, sulfur atom —S—, methylene group —CH$_2$—, amino group —NH—, methylamino group —N(CH$_3$)—, ethylamino group —N(CH$_2$ CH$_3$)—, propylamino group —N(CH$_2$ CH$_2$ CH$_3$)—, butylamino group —N(CH$_2$ CH$_2$ CH$_2$ CH$_3$)—, acetylamino group —N(COCH$_3$)—, formylamino group —N(CHO)—, propanoylamino group —N(COCH$_2$ CH$_3$)— and benzoylamino group —N(COPh)—.

Examples of B, which is also a partial structure of the general formula (I), include —CH$_2$ CH$_2$—, —CH$_2$ CH$_2$ CH$_2$—, —CH$_2$ CH$_2$ CH$_2$ CH$_2$—, —CH$_2$ CH(OH)CH$_2$—, —CH$_2$CH(OCOCH$_3$)CH$_2$—, —CH$_2$ CH(OCHO)CH$_2$—, —CH$_2$ CH(NH$_2$)CH$_2$—, —CH$_2$ CH(NHCH$_3$)CH$_2$—, —CH$_2$ CH(NMe$_2$)CH$_2$—, —CH$_2$CH(NHCH$_2$CH$_3$)CH$_2$—, —CH$_2$CH(OCH$_3$)CH$_2$—, —CH$_2$CH(OCH$_2$CH$_3$)CH$_2$—, —COCH$_2$CH$_2$—, —COCH$_2$CH$_2$CH$_2$— and —COCH$_2$CH$_2$CH$_2$CH$_2$—.

Examples of C, which also is a partial structure of the general formula (I), include a piperazine ring, homopiperazine ring, N,N'-dimethylethylenediamine, N,N'-diethylethylenediamine, ethylamine, propylamine, N-methylpropylamine and a piperidine ring.

Examples of D, which is also a partial structure of the general formula (I), include a diphenylmethyl group, benzyl group, (4-pyridyl)methyl group, (3-pyridyl)methyl group, (2-pyridyl)methyl group, phenyl-(2-pyridyl)methyl group, phenyl-(3-pyridyl)methyl group, phenyl-(4-pyridyl)methyl group, di(2-pyridyl)methyl group, di(4-pyridyl)methyl group, diphenyl-hydroxymethyl group, triphenylmethyl group, (4-chlorophenyl)-phenylmethyl group, bis(4-chlorophenyl)methyl group, (4-fluorophenyl)-phenylmethyl group, bis(4 fluorophenyl)methyl group, (4-methoxyphenyl)phenylmethyl group, bis(4-methoxyphenyl)methyl group, (4-hydroxyphenyl)phenylmethyl group, bis(4-hydroxyphenyl)methyl group, (4-dimethylaminophenyl)-phenylmethyl group, (2,3-dimethoxyphenyl)-(3,4-dimethoxyphenyl)methyl group, bis(4-dimethylaminophenyl)methyl group, 5-fluorenyl group, 9,10-dihydro-9-anthrasenyl group, 5-dibenzosuberanyl group, 6,11-dihydrodibenzo[b,e]oxepine-11-yl group, 5-dibenzosuberenyl group, 5-xanthenyl group, diphenylmethoxy group, 5-dibenzosuberanyloxy group, phenyl-(2-pyridyl)methoxy group, phenyl-(3-pyridyl)methoxy group, phenyl-(4-pyridyl)methoxy group, di(2-pyridyl)methoxy group, di(3-pyridyl)methoxy group, di(4-pyridyl)methoxy group, bis(4-methoxyphenyl)methoxy group, bis(4-hydroxyphenyl)methoxy group, bis(4-dimethylaminophenyl)methoxy group, (2,3-dimethoxyphenyl)-(3,4-dimethoxyphenyl)methoxy group, 6,11-dihydrodibenzo[b,e]oxepine-11-yloxy group, 5-dibenzosuberenyloxy group, 5-xanthenyloxy group, 2,2-diphenylethyl group, 2,2-di(2-pyridyl)ethyl group, 2,2-di(4-pyridyl)ethyl group, 2-phenyl-2-(2-pyridyl)ethyl group, 2-phenyl-2-(3-pyridyl)ethyl group, 2-phenyl-2-(4-pyridyl)ethyl group, 2,2-di-phenyl-2-hydroxyethyl group, 2-(4-chlorophenyl)-2-phenylethyl group, 2,2-bis(4-chlorophenyl)ethyl group, 2-(4-methoxyphenyl)-2-phenylethyl group, 2,2-bis(4-methoxyphenyl)ethyl group, 2-(4-hydroxyphenyl)-2-phenylethyl group, 2,2-bis(4-hydroxyphenyl)ethyl group, 2-(4-dimethylaminophenyl)-2-phenylethyl group, 2-(2,3-dimethoxyphenyl)-2-(3,4 dimethoxypheny)ethyl group, (5-dibenzosuberanyl)methyl group, 2,2-diphenylacetyl group, 2-phenylacetyl group, 2-(4-pyridyl)acetyl group, 2-(3-pyridyl)acetyl group, 2-(2-pyridyl)acetyl group, 2-phenyl-2-(2-pyridyl)acetyl group, 2-phenyl-2-(3-pyridyl)acetyl group, 2-phenyl-2-(4-pyridyl)acetyl group, 2,2-di(2-pyridyl)acetyl group, 2,2-di(4-pyridyl)acetyl group, 2,2,2-triphenylacetyl group, 2-(4-chlorophenyl)-2-phenylacetyl group, 2,2-bis(4-chlorophenyl)acetyl group, 2-(4-fluorophenyl)-2-phenylacetyl group, 2,2-bis(4-fluorophenyl)acetyl group, 2-(4-methoxyphenyl)-2-phenylacetyl group, 2,2-bis(4-methoxyphenyl)acetyl group, 2-(4-hydroxyphenyl)-2-phenylacetyl group, 2,2-bis(4-hydroxyphenyl)acetyl group, 2-(4-dimethylaminophenyl)-2-phenylacetyl group, 2,2-bis(4-dimethylaminophenyl)acetyl group, 2-(2,3-dimethoxyphenyl)-2-(3,4-dimethoxyphenyl)acetyl group, dibenzosuberane-5-carbonyl group, fluorene-5-carbonyl group, 6,11-dihydrobenzo[b,e]oxepine-11-carbonyl group, dibenzosuberene-5-carbonyl group, 5-xanthenecarbonyl group, 3,3-diphenylpropyl group, 3-(dibenzosuberane-5-yl)ethyl group, (diphenylmethyl)amino group, 5-dibenzosuberanylamino group, N,N-diphenylamino group, N-phenyl—N-(2-pyridyl)amino group, N-phenyl—N-(3-pyridyl)amino group, N-phenyl—N-(4 pyridyl)amino group, N,N-bis(4-chlorophenyl)amino group, N,N-bis(4-fluorophenyl)amino group, N,N-bis(4-methoxyphenyl)amino group, N,N-bis(4-hydroxyphenyl)amino group, 9,10-dihydroacridine-10-yl group, 10,11-dihydro-dibenzo[b,f]-azepine-5-yl group, dibenzo[b,f]azepine-5-yl group, N,N-diphenylcarbamoyl group, N-phenyl—N-(2-pyridyl)carbamoyl group, N-phenyl—N-(3-pydidyl)carbamoyl group, N-phenyl—N-(4 pydidyl)carbamoyl group, N,N-bis(4-chlorophenyl)carbamoyl group, N,N-bis(4-fluorophenyl)carbamoyl group, N,N-bis(4-methoxyphenyl)carbamoyl group, N,N-bis(4-hydroxyphenyl)carbamoyl group, 9,10-dihydroacridine-10-carbonyl group, 10,11-dihydro-dibenzo[b,f]azepine-5-carbonyl group, dibenzo[b,- f]azepine-5-carbonyl group and diphenylmethylene group.

Specific examples of compounds represented by general formula (I) include:

5-[3-(4-diphenylmethylpiperazine-1-yl)-2-hydroxyl-Propoxy]quinoline,
5-[3-(4-(dibenzosuberane-5-yl)piperazine-1-yl)-2 hydroxylpropoxy]quinoline,
5-[3-(4-diphenylmethylpiperazine-1-yl)-2-hydroxylpropoxy]-2-methylquinoline,
5-[3-(4-diphenylmethylpiperazine-1-yl)-2-hydroxylpropoxy]-3-methylquinoline,
5-[3-(4-diphenylmethylpiperazine-1-yl)-2-hydroxylpropoxy]-4-methylquinoline,
5-[3-(4-diphenylmethylpiperazine-1-yl)-2-hydroxylpropoxy]-6-methylquinoline,
5-[3-(4-diphenylmethylpiperazine-1-yl)-2-hydroxylpropoxy]-7-methylquinoline,
5-[3-(4-diphenylmethylpiperazine-1-yl)-2-hydroxylpropoxy]-8-methylquinoline,
5-[3-(4-(dibenzosuberane-5-yl)piperazine-1-yl)-2-hydroxylpropoxy]-2-methylquinoline,
5-[3-(4-(dibenzosuberane-5-yl)piperazine-1-yl)-2 hydroxylpropoxy]-3-methylquinoline,
5-[3-(4-(dibenzosuberane-5-yl)piperazine-1-yl)-2 hydroxylpropoxy]-4-methylquinoline,
5-[3-(4-(dibenzosuberane-5-yl)piperazine-1-yl)-2 hydroxylpropoxy]-6-methylquinoline,
5-[3-(4-(dibenzosuberane-5-yl)piperazine-1-yl)-2 hydroxylpropoxy]-7-methylquinoline,
5-[3-(4-(dibenzosuberane-5-yl)piperazine-1-yl)-2 hydroxylpropoxy]-8-methylquinoline,
5-[3-(4-diphenylmethylpiperazine-1-yl)-2-hydroxylpropoxy]-2-methoxyquinoline,
5-[3-(4-diphenylmethylpiperazine-1-yl)-2-hydroxylpropoxy]-3-methoxyquinoline,
5-[3-(4-diphenylmethylpiperazine-1-yl)-2-hydroxylpropoxy]-4-methoxyquinoline,
5-[3-(4-diphenylmethylpiperazine-1-yl)-2-hydroxylpropoxy]-6-methoxyquinoline,
5-[3-(4-diphenylmethylpiperazine-1-yl)-2-hydroxylpropoxy]-7-methoxyquinoline,
5-[3-(4-diphenylmethylpiperazine-1-yl)-2-hydroxylpropoxy]-8-methoxyquinoline,
5-[3-(4-(dibenzosuberane-5-yl)piperazine-1-yl)-2 hydroxylpropoxy]-2-methoxyquinoline,
5-[3-(4-(dibenzosuberane-5-yl)piperazine-1-yl)-2 hydroxylpropoxy]-3-methoxyquinoline,
5-[3-(4-(dibenzosuberane-5-yl)piperazine-1-yl)-2 hydroxylpropoxy]-4-methoxyquinoline,
5-[3-(4-(dibenzosuberane-5-yl)piperazine-1-yl)-2 hydroxylpropoxy]-6-methoxyquinoline,
5-[3-(4-(dibenzosuberane-5-yl)piperazine-1-yl)-2 hydroxylpropoxy]-7-methoxyquinoline,
5-[3-(4-(dibenzosuberane-5-yl)piperazine-1-yl)-2 hydroxylpropoxy]-8-methoxyquinoline,
2-ethyl-5-[3-(4-diphenylmethylpiperazine-1-yl)-2 hydroxylpropoxy]quinoline,
2-ethyl-5-[3-(4-(dibenzosuberane-5-yl)piperazine-1-yl)-2-hydroxylpropoxy]quinoline,
5-[3-(4-diphenylmethylpiperazine-1-yl)-2-hydroxylpropoxy]-2-propylquinoline,
5-[3-(4-(dibenzosuberane-5-yl)piperazine-1-yl)-2-hydroxylpropoxy]-2-propylquinoline,
2-butyl-5-[3-(4-diphenylmethylpiperazine-1-yl)-2-hydroxylpropoxy]quinoline,
2-butyl-5-[3-(4-(dibenzosuberane-5-yl)piperazine-1-yl)-hydroxylpropoxy]quinoline,
2,4-dimethyl-5-[3-(4-diphenylmethylpiperazine-1-yl)-2-hydroxylpropoxy]quinoline,
2,4-dimethyl-5-[3-(4-(dibenzosuberane-5-yl)piperazine-1-yl)-2-hydroxylpropoxy]quinoline,
5-[3-(4-diphenylmethylpiperazine-1-yl)-2-hydroxylpropoxy]-7-nitroquinoline,
5-[3-(4-diphenylmethylpiperazine-1-yl)-2-hydroxylpropoxy]-8-nitroquinoline,
5-[3-(4-(dibenzosuberane-5-yl)piperazine-1-yl)-2 hydroxylpropoxy]-7-nitroquinoline,
5-[3-(4-(dibenzosuberane-5-yl)piperazine-1-yl)-2 hydroxylpropoxy]-8-nitroquinoline,
2-chloro-5-[3-(4-diphenylmethylpiperazine-1-yl)-2 hydroxylpropoxy]quinoline,
3-chloro-5-[3-(4-diphenylmethylpiperazine-1-yl)-2 hydroxylpropoxy]quinoline,
4-chloro-5-[3-(4-diphenylmethylpiperazine-1-yl)-2 hydroxylpropoxy]quinoline,
6-chloro-5-[3-(4-diphenylmethylpiperazine-1-yl)-2 hydroxylpropoxy]quinoline,
7-chloro-5-[3-(4-diphenylmethylpiperazine-1-yl)-2 hydroxylpropoxy]quinoline,
8-chloro-5-[3-(4-diphenylmethylpiperazine-1-yl)-2 hydroxylpropoxy]quinoline,
2-chloro-5-[3-(4-(dibenzosuberane-5-yl)piperazine-1-yl)-2-hydroxylpropoxy]quinoline,
3-chloro-5-[3-(4-(dibenzosuberane-5-yl)piperazine-1-yl)-2-hydroxylpropoxy]quinoline,
4-chloro-5-[3-(4-(dibenzosuberane-5-yl)piperazine-1-yl)-2-hydroxylpropoxy]quinoline,
6-chloro-5-[3-(4-(dibenzosuberane-5-yl)piperazine-1-yl)-2-hydroxylpropoxy]quinoline,
7-chloro-5-[3-(4-(dibenzosuberane-5-yl)piperazine-1-yl)-2-hydroxylpropoxy]quinoline,
8-chloro-5-[3-(4-(dibenzosuberane-5-yl)piperazine-1-yl)-2-hydroxylpropoxy]quinoline,
5-[3-(4-diphenylmethylpiperazine-1-yl)-2-hydroxylpropoxy]-2-trifluoromethylquinoline,
5-[3-(4-diphenylmethylpiperazine-1-yl)-2-hydroxylpropoxy]-4-trifluoromethylquinoline,
5-[3-(4-(dibenzosuberane-5-yl)piperazine-1-yl)-2 hydroxylpropoxy]-2-trifluoromethylquinoline,
5-[3-(4-(dibenzosuberane-5-yl)piperazine-1-yl)-2 hydroxylpropoxy]-4-trifluoromethylquinoline,
2,4-bis(trifluoromethyl)-5-[3-(4-diphenylmethylpiperazine-1-yl)-2-hydroxylpropoxy]quinoline,
2,4-bis(trifluoromethyl)-5-[3-(4-(dibenzosuberane-5-yl)piperazine-1-yl)-2-hydroxylpropoxy]quinoline,
5-[3-(4-diphenylmethylpiperazine-1-yl)-2-hydroxylpropoxy]-2-fluoroquinoline,
5-[3-(4-diphenylmethylpiperazine-1-yl)-2-hydroxylpropoxy]-4-fluoroquinoline,
5-[3-(4-(dibenzosuberane-5-yl)piperazine-1-yl)-2-hydroxylpropoxy]-2-fluoroquinoline,
5-[3-(4-(dibenzosuberane-5-yl)piperazine-1-yl)-2 hydroxylpropoxy]-4-fluoroquinoline,
2-bromo-5-[3-(4-diphenylmethylpiperazine-1-yl)-2 hydroxylpropoxy]quinoline,
3-bromo-5-[3-(4-diphenylmethylpiperazine-1-yl)-2 hydroxylpropoxy]quinoline,
4-bromo-5-[3-(4-diphenylmethylpiperazine-1-yl)-2 hydroxylpropoxy]quinoline,
2-bromo-5-[3-(4-(dibenzosuberane-5-yl)piperazine-1-yl)-2-hydroxylpropoxy]quinoline,
3-bromo-5-[3-(4-(dibenzosuberane-5-yl)piperazine-1-yl)-2-hydroxylpropoxy]quinoline,
4-bromo-5-[3-(4-(dibenzosuberane-5-yl)piperazine-1-yl)-2-hydroxylpropoxy]quinoline, 2-amino-5-[3-(4-diphenylmethylpiperazine-1-yl)-2-hydroxylpropoxy]quinoline,
2-amino-5-[3-(4-(dibenzosuberane-5-yl)piperazine-1-yl)-2-hydroxylpropoxy]quinoline,
5-[3-(4-diphenylmethylpiperazine-1-yl)-2-hydroxylpropoxy]-2-methylaminoquinoline,
5-[3-(4-(dibenzosuberane-5-yl)piperazine-1-yl)-2-hydroxylpropoxy]-2-methylaminoquinoline,
2-dimethylamino-5-[3-(4-diphenylmethylpiperazine-1-yl)-2-hydroxylpropoxy]quinoline,
2-dimethylamino-5-[3-(4-(dibenzosuberane-5-yl)piperazine-1-yl)-2-hydroxylpropoxy]quinoline,
2-ethoxy-5-[3-(4-diphenylmethylpiperazine-1-yl)-2-hydroxylpropoxy]quinoline,
2-ethoxy-5-[3-(4-(dibenzosuberane-5-yl)piperazine-1-yl)-2-hydroxylpropoxy]quinoline,
2-cyano-5-[3-(4-diphenylmethylpiperazine-1-yl)-2-hydroxylpropoxy]quinoline,
2-cyano-5-[3-(4-(dibenzosuberane-5-yl)piperazine-1-yl)-2-hydroxylpropoxy]quinoline,
5-[3-(4-diphenylmethylpiperazine-1-yl)-2-hydroxylpropoxy]-8-hydroxyquinoline,
5[3-(4-(dibenzosuberane-5-yl)piperazine-1-yl)-2-hydroxylpropoxy]-8-hydroxyquinoline,
5-[3-(4-diphenylmethylpiperazine-1-yl)-2-hydroxylpropylthio]quinoline,
5-[3-(4-(dibenzosuberane-5-yl)piperazine-1-yl)-2-hydroxylpropylthio]quinoline,
5-[4-(4-diphenylmethylpiperazine-1-yl)butyl]quinoline,
5-[3-(4-(dibenzosuberane-5-yl)piperazine-1-yl)butyl]quinoline,
5-[3-(4-diphenylmethylpiperazine-1-yl)-2-hydroxypropylamino]quinoline,
5[3-(4-(dibenzosuberane-5-yl)piperazine-1-yl)-2-hydroxypropylamino]quinoline,
N-[3-(4-diphenylmethylpiperazine-1-yl)-2-hydroxypropyl]-N-methyl-5-quinolineamine,
N-[3-(4-(dibenzosuberane-5-yl)piperazine-1-yl)-2-hydroxypropyl]-N-methyl-5-quinolineamine,
N-[3-(4-diphenylmethylpipera-zine-1-yl)-2-hydroxypropyl]-N-acetyl-5-quinolineamine,
N-[3-(4-(dibenzosuberane-5-yl)piperazine-1-yl)-2-hydroxypropyl]-N-acetyl-5-quinolineamine,
5-[2-(4-diphenylmethylpiperazine-1-yl)ethoxy]quinoline,
5-[2-(4-(dibenzosuberane-5-yl)piperazine-1-yl)ethoxy]quinoline,
5-[4-(4-diphenylmethylpiperazine-1-yl)butoxy]quinoline,
5-[4-(4-(dibenzosuberane-5-yl)piperazine-1-yl)butoxy]quinoline,
5-[3-(4-diphenylmethylpiperazine-1-yl)propoxy]quinoline,
5-[3-(4-(dibenzosuberane-5-yl)piperazine-1-yl)propoxy]quinoline,
5-[2-acetoxy-3-(4-diphenylmethylpiperazine-1-yl)propoxy]quinoline,
5-[2-acetoxy-3-(4-(dibenzosuberane-5-yl)piperazine-1-yl)propoxy]quinoline,
5-[2-amino-3-(4-diphenylmethylpiperazine-1-yl)propoxy]quinoline,
5-[2-amino-3-(4-(dibenzosuberane-5-yl)piperazine-1-yl)propoxy] quinoline,
5-[3-(4-diphenylmethylpiperazine-1-yl)-2-methylaminopropoxy]quinoline,
5-[3-(4-(dibenzosuberane-5-yl)piperazine-1-yl)-2-methylaminopropoxy]quinoline,
5-[3-(4-diphenylmethylpiperazine-1-yl)-2-methoxypropoxy]quinoline,
5-[3-(4-(dibenzosuberane-5-yl)piperazine-1-yl)-2-methoxypropoxy]quinoline,
5-[3-(4-diphenylmethylpiperazine-1-yl)-2-propionamido]quinoline,
5-[3-(4-(dibenzosuberane-5-yl)piperazine-1-yl)propionamido]quinoline,
5-[3-(4-diphenylmethylpiperazine-1-yl)-N-methylpropionamido]quinoline,
5-[3-(4-(dibenzosuberane-5-yl)piperazine-1-yl)-N-propionamido]quinoline,
5-[3-(4-diphenylmethylhomopiperazine-1-yl)-2-hydroxypropoxy]quinoline,
5-[3-(4-(dibenzosuberane-5-yl)homopiperazine-1-yl)-2-hydroxypropoxy]quinoline,
5-(3-[N-(2-(N-diphenylmethyl-N-methylamino)ethyl)-N-methylamino]-2-hydroxypropoxy)quinoline,
5-(3-(N-[2-(N-(dibenzosuberane-5-yl)-N-methylamino)ethyl]-N-methylamino)-2-hydroxypropoxy)quinoline,
5-[3-(4-(diphenyl-hydroxymethyl)piperidine-1-yl)-2-hydroxypropoxy]quinoline,
5-[3-(4-(diphenylmethylene)piperidine-1-yl)-2-hydroxypropoxy]quinoline,
5-[3-(4-diphenylmethylpiperidine-1-yl)-2-hydroxypropoxy]quinoline,
5-[3-(4-(diphenyl-hydroxymethyl)piperidine-1-yl)-2-hydroxypropoxy]-2-quinoline,
5-[3-(4-(phenyl-2-pyridylmethyl)piperazine-1-yl)-2-hydroxypropoxy]quinoline,
5-[3-(4-(phenyl-3-pyridylmethyl)piperazine-1-yl)-2-hydroxypropoxy]quinoline,
5-[3-(4-(phenyl-4-pyridylmethyl)piperazine-1-yl)-2-hydroxypropoxy]quinoline,
5-(3-[4-(di-(2-pyridyl)methyl)piperazine-1-yl]-2-hydroxypropoxy)quinoline,
5-(3-[4-(di-(3-pyridyl)methyl)piperazine-1-yl]-2-hydroxypropoxy)quinoline,
5-(3-[4-(di-(4-pyridyl)methyl)piperazine-1-yl]-2-hydroxypropoxy)quinoline,
5-(3-[4-(bis(4-chlorophenyl)methyl)piperazine-1-yl]-2-hydroxypropoxy)quinoline,
5-(3-[4-(bis(4-fluorophenyl)methyl)piperazine-1-yl]-2-hydroxypropoxy)quinoline,
5-(3-[4-((4-chlorophenyl)-phenylmethyl)piperazine-1-yl] -2-hydroxypropoxy)quinoline,
5-(3-[4-(bis(4-methoxyphenyl)methyl)piperazine-1-yl]-2-hydroxypropoxy)quinoline,
5-(3-[4-(bis(4-hydroxyphenyl)methyl)piperazine-1-yl]-2-hydroxypropoxy)quinoline,
5-(3-[4-(bis(4-dimethylaminophenyl)methyl)piperazine-1-yl]-2-hydroxypropoxy)quinoline,
5-(3-[4-((2,3-dimethylphenyl)-(3,4-dimethoxyphenyl)methyl)piperazine-1-yl]-2-hydroxypropoxy)quinoline,
5-[3-(4-(fluorene-5-yl)piperazine-1-yl)-2-hydroxypropoxy]quinoline,
5-[3-(4-(9,10-dihydro-9-anthracenyl)piperazine-1-yl)-2-hydroxypropoxy]quinoline,
5-[3-(4-(6,11-dihydrodibenzo[b,e]oxepine-11-yl)piperazine-1-yl)-2-hydroxypropoxy]quinoline,
5-[3-(4-(dibenzosuberene-5-yl)piperazine-1-yl)-2-hydroxypropoxy]quinoline,
5-[3-(4-(xanthene-5-yl)piperazine-1-yl)-2-hydroxypropoxy]quinoline,
5-[3-(4-(diphenylmethoxy)piperidine-1-yl)-2-hydroxypropoxy]quinoline, 5-[3-(4-(dibenzosuberane-5-yloxy)piperazine-1-yl)-2-hydroxypropoxy]quinoline,
5-[3-(4-(phenyl-2-pyridylmethoxy)piperidine-1-yl)-2-hydroxypropoxy]quinoline,
5-[3-(4-(phenyl-3-pyridylmethoxy)piperidine-1-yl)-2-hydroxypropoxy]quinoline,
5-[3-(4-(phenyl-4-pyridylmethoxy)piperidine-1-yl)-2-hydroxypropoxy]quinoline,
5-(3-[4-(di(2-pyridyl)methox-y)piperidine-1-yl]-2-hydroxypropoxy)quinoline,
5-(3-[4-(di(3-pyridyl)methoxy)piperidine-1-yl]-2-hydroxypropoxy)quinoline,
5-(3-[4-(di(4-pyridyl)methoxy)piperidine-1-yl]-2-hydroxypropoxy)quinoline,
5-(3-[4-(bis(4-chlorophenyl)methoxy)piperidine-1-yl]-2-hydroxypropoxy)quinoline,
5-(3-[4-(bis(4-fluorophenyl)methoxy)piperidine-1-yl]-2-hydroxypropoxy)quinoline,
5-(3-[4-((4-chlorophenyl)-phenylmethoxy)piperidine-1-yl]-2-hydroxypropoxy)quinoline,
5-(3-[4-(bis(4-methoxyphenyl)-methoxy)piperidine-1-yl]-2-hydroxypropoxy)quinoline,
5-(3-[4-(bis(4-methoxyphenyl)methoxy)piperidine-1-yl]-2-hydroxypropoxy)quinoline,
5-(3-[4-(bis(4-dimethylaminophenyl)methoxy)piperidine-1-yl]-2-hydroxypropoxy)quinoline,
5-(3-[4-((2,3-dimethoxyphenyl)-(3,4-dimethoxyphenyl)methoxy)piperidine-1-yl]-2-hydroxyproPoxy)quinoline,
5-(3-[4-(9,10-dihydro-9-anthracenyloxy)piperidine-1-yl]-2-hydroxypropoxy)quinoline,
5-(3-[4-(6,11-dihydrodibenzo[b,e]oxepine-11-yloxy)-piperidine-1-yl]-2-hydroxypropoxy)quinoline,
5-[3-(4-(dibenzosuberene-5-yloxy)piperidine-1-yl)-2-hydroxypropoxy]quinoline,
5-[3-(4-(xanthene-5-yloxy)piperidine-1-yl)-2-hydroxypropoxy]quinoline,
5-[3-(4-(2,2-diphenylethyl)piperazine-1-yl)-2-hydroxypropoxy]quinoline,
5-[3-(4-(dibenzosuberane-5-yl)methylpiperazine-1-yl)-2-hydroxypropoxy]quinoline,
5-(3-[4-(2-phenyl-2-(2-pyridyl)ethyl)piperazine-1-yl]-2-hydroxypropoxy)quinoline,
5-(3-[4-(2-phenyl-2-(3-pyridyl)ethyl)piperazine-1-yl]-2-hydroxypropoxy)quinoline,
5-(3-[4-(2-phenyl-2-(4-pyridyl)ethyl)piperazine-1-yl]-2-hydroxypropoxy)quinoline,
5-(3-[4-(2,2-di(2-pyridyl)ethyl)piperazine-1-yl]-2-hydroxypropoxy)quinoline,
5-(3-[4-(2,2-di(3-pyridyl)ethyl)piperazine-1-yl]-2-hydroxypropoxy)quinoline,
5-(3-[4-(2,2-di(4-pyridyl)ethyl)piperazine-1-yl]-2-hydroxypropoxy)quinoline,
5-(3-[4-(2,2-bis(4-chlorophenyl)ethyl)piperazine-1-yl]-2-hydroxypropoxy)quinoline,
5-(3-[4-(2,2-bis(4-fluorophenyl)ethyl)piperazine-1-yl]-2-hydroxypropoxy)quinoline,
5-(3-[4-(2,2-(4-chlorophenyl)-phenylethyl)piperazine-1-yl]-2-hydroxypropoxy)quinoline,
5-(3-[4-(2,2-bis(4-methoxyphenyl)ethyl)piperazine-1-yl]-2-hydroxypropoxy)quinoline,
5-(3-[4-(2,2-bis(4-hydroxyphenyl)ethyl)piperazine-1-yl]-2-hydroxypropoxy)quinoline,
5-(3-[4-(2,2-bis(4-dimethylaminophenyl)ethyl)piperazine-1-yl]-2-hydroxypropoxy)quinoline,
5-(3-[4-(2-(2,3-dimethoxyphenyl)-2-(3,4-dimethoxyphenyl)ethyl)piperazine-1-yl]-2-hydroxypropoxy)quinoline,
5-(3-[4-(fluorene-5-yl)methylpiperazine-1-yl]-2-hydroxypropoxy)quinoline
5-(3-[4-(9,10-dihydro-9-anthracenyl)methylpiperazine-1-yl]-2-hydroxypropoxy)quinoline,
5-[3-(4-(6,11-dihydrodibenzo[b,e]oxepine-11-yl)methylpiperazine-1-yl)-2-hydroxypropoxy]quinoline,
5-[3-(4-(dibenzosuberene-5-yl)methylpiperazine-1-yl)-2-hydroxypropoxy]quinoline,
5-[3-(4-(xanthene-5-yl)methylpiperazine-1-yl)-2-hydroxypropoxy]quinoline,
5-[3-(4-(diphenylacetyl)piperidine-1-yl)-2-hydroxypropoxy]quinoline,
5-[3-(4-(dibenzosuberane-5-carbonyl)piperidine-1-yl)-2-hydroxypropoxy] quinoline,
5-[3-(4-(phenyl-2-pyridylacetyl)piperidine-1-yl)-2-hydroxypropoxy]quinoline,
5-[3-(4-(phenyl-3-pyridylacetyl)piperidine-1-yl)-2-hydroxypropoxy]quinoline,
5-[3-(4-(phenyl-4-pyridylacetyl)piperidine-1-yl)-2-hydroxypropoxy]quinoline,
5-(3-[4-(di-(2-pyridyl)acetyl)piperidine-1-yl]-2-hydroxypropoxy)quinoline,
5-(3-[4-(di-(3-pyridyl)acetyl)piperidine-1-yl]-2-hydroxypropoxy)quinoline,
5-(3-[4-(di-(4-pyridyl)acetyl)piperidine-1-yl]-2-hydroxypropoxy)quinoline,
5-(3-[4-(bis(4-chlorophenyl)acetyl)piperidine-1-yl]-2-hydroxypropoxy)quinoline,
5-(3-[4-(bis(4-fluorophenyl)acetyl)piperidine-1-yl]-2-hydroxypropoxy)quinoline,
5-(3-[4-((4-chlorophenyl)-phenylacetyl)piperidine-1-yl]-2-hydroxypropoxy)quinoline,
5-(3-[4-(bis(4-methoxyphenyl)acetyl)piperidine-1-yl]-2-hydroxypropoxy)quinoline,
5-(3-[4-(bis(4-hydroxyphenyl)acetyl)piperidine-1-yl]-2-hydroxypropoxy)quinoline,
5-(3-[4-(bis(4-dimethylaminophenyl)acetyl)piperidine-1-yl]-2-hydroxypropoxy)quinoline,
5-(3-[4-((2,3-dimethoxyphenyl)-(3,4-dimethoxyphenyl)acetyl)piperidine-1-yl]-2-hydroxypropoxy)quinoline,
5-[3-(4-(9,10-dihydro-anthracenyl-9-carbonyl)piperidine-1-yl)-2-hydroxypropoxy]quinoline,
5-(3-[4-(6,11-dihydrodibenze[b,e]oxepine-11-carbonyl)-piperidine-1-yl]-2-hydroxypropoxy)quinoline,
5-[3-(4-(dibenzosuberene-5-carbonyl)piperidine-1-yl)-2-hydroxypropoxy]quinoline,
5-[3-(4-(xanthene-5-carbonyl)piperidine-1-yl)-2-hydroxypropoxy]quinoline,
5-[3-(4-(2,2-diphenylacetyl)piperazine-1-yl)-2-hydroxypropoxy]quinoline,
5-(3-[4-(dibenzosuberane-5-carbonyl)piperazine-1-yl)-2-hydroxypropoxy]quinoline,
5-(3-[4-(2-phenyl-2-(2-pyridyl)acetyl)piperazine-1-yl]-2-hydroxypropoxy)quinoline,
5-(3-[4-(2-phenyl-2-(3-pyridyl)acetyl)piperazine-1-yl]-2-hydroxypropoxy)quinoline,
5-(3-[4-(2-phenyl-2-(4-pyridyl)acetyl)piperazine-1-yl]-2-hydroxypropoxy)quinoline,
5-(3-[4-(2,2-di-(2-pyridyl)acetyl)piperazine-1-yl]-2-hydroxypropoxy)quinoline,
5-(3-[4-( 2,2-di(3-pyridyl)acetyl)piperazine-1-yl]-2-hydroxypropoxy)quinoline,
5-(3-[4-( 2,2-di(4-pyridyl)acetyl)piperazine-1-yl]-2-hydroxypropoxy)quinoline,
5-(3-[4-(2,2-bis(4-chlorophenyl)acetyl)piperazine-1-yl]-2-hydroxypropoxy)quinoline, 5-(3-[4-(2,2-bis(4-fluorophenyl)acetyl)piperazine-1-yl]-2-hydroxypropoxy)quinoline,
5-(3-[4-(2-(4-chlorophenyl)-2-phenylacetyl)piperazine-1-yl]-2-hydroxypropoxy)quinoline,
5-(3-[4-(2,2-bis(4-methoxyphenyl)acetyl)piperazine-1-yl]-2-hydroxypropoxy)quinoline,
5-(3-[4-(2,2-bis(4-hydroxyphenyl)acetyl)piperazine-1-yl]-2-hydroxypropoxy)quinoline,
5-(3-[4-(2,2-bis(4-dimethylaminophenyl)acetyl)piperazine-1-yl]-2-hydroxypropoxy)quinoline,
5-(3-[4-(2-(2,3-dimethoxyphenyl)-2-(3,4-dimethoxyphenyl)acetyl)piperazine-1-yl]-2-hydroxypropoxy)quinoline,
5-[3-(4-(fluorene-5-carbonyl)piperazine-1-yl)-2-hydroxypropoxy]quinoline,
5-[3-(4-(9,10-dihydroanthracenyl-9-carbonyl)piperazine-1-yl)-2-hydroxypropoxy]quinoline,
5-[3-(4-(6,11-dihydrodibenzo[b,e]oxepine-11-carbonyl)piperazine-1-yl)-2-hydroxypropoxy]quinoline,
5-[3-(4-(dibenzosuberene-5-carbonyl)piperazine-1-yl)-2-hydroxypropoxy]quinoline,
5-[3-(4-(xanthene-5-carbonyl)piperazine-1-yl)-2-hydroxypropoxy]quinoline,
5-[3-(4-(3,3-diphenylpropyl)piperazine-1-yl)-2-hydroxypropoxy]quinoline,
5-(3-[4-(2-(5-dibenzosuberanyl)ethyl)piperazine-1-yl]-2-hydroxypropoxy)quinoline,
5-[3-(4-(diphenylmethylamino)piperidine-1-yl)-2-hydroxypropoxy)quinoline,
5-(3-[4-((5-dibenzosuberanyl)amino)piperidine-1-yl]-2-hydroxypropoxy)quinoline,
5-[3-(4-(N,N-diphenylamino)piperidine-1-yl)-2-hydroxypropoxy]quinoline,
5-(3-[4-(N-diphenyl-N-(2-pyridyl)amino)piperidine-1-yl]-2-hydroxypropoxy)quinoline,
5-(3-[4-(N-diphenyl-N-(3-pyridyl)amino)piperidine-1-yl]-2-hydroxypropoxy)quinoline,
5-(3-[4-(N-phenyl-N-(4-pyridyl)amino)piperidine-1-yl]-2-hydroxypropoxy)quinoline,
5-(3-[4-(N,N-bis(4-chlorophenyl)amino)piperidine-1-yl]-2-hydroxypropoxy)quinoline,
5-(3-[4-(N,N-bis(4-fluorophenyl)amino)piperidine-1-yl]-2-hydroxypropoxy)quinoline,
5-(3-[4-(N,N-bis(4-methoxyphenyl)amino)piperidine-1-yl]-2-hydroxypropoxy)quinoline,
5-(3-[4-(N,N-bis(4-hydroxyphenyl)amino)piperidine-1-yl]-2-hydroxypropoxy)quinoline,
5-[3-(4-(9,10-dihydroacridine-10-yl)piperidine-1-yl)-2-hydroxypropoxy] quinoline,
5-[3-(4-(10,11-dihydrodibenzo[b,f]azepine-5-yl)piperidine-1-yl)-2-hydroxypropoxy)quinoline,
5-[3-(4-(dibenzo[b,f]azepine-5-yl)piperidine-1-yl)-2-hydroxypropoxy)quinoline,
5-[3-(4-(N,N-diphenylcarbamoyl)piperidine-1-yl)-2-hydroxypropoxy]quinoline,
5-(3-[4-(N-phenyl-N-(2-pyridyl)carbamoyl)piperidine-1-yl]-2-hydroxypropoxy)quinoline,
5-(3-[4-(N-phenyl-N-(3-pyridyl)carbamoyl)piperidine-1-yl]-2-hydroxypropoxy)quinoline,
5-(3-[4-(N-phenyl-N-(4-pyridyl)carbamoyl)piperidine-1-yl]-2-hydroxypropoxy)quinoline,
5-(3-[4-(N,N-bis(4-chlorophenyl)carbamoyl)piperidine-1-yl]-2-hydroxypropoxy)quinoline,
5-(3-[4-(N,N-bis(4-fluorophenyl)carbamoyl)piperidine-1-yl]-2-hydroxypropoxy)quinoline,
5-(3-[4-(N,N-bis(4-methoxyphenyl)carbamoyl)piperidine-1-yl]-2-hydroxypropoxy)quinoline,
5-(3-[4-(N,N-bis(4-hydroxyphenyl)carbamoyl)piperidine-1-yl]-2-hydroxypropoxy)quinoline,
5-(3-[4-(9,10-dihydroacridine-10-carbonyl)piperidine-1-yl]-2-hydroxypropoxy)quinoline,
5-[3-(4-(10,11-dihydrodibenzo[b,f]azepine-5-carbonyl)-piperidine-1-yl)-2-hydroxypropoxy]quinoline,
5-[3-(4-(dibenzo[b,f]azepine-5-carbonyl)piperidine-1-yl)-2-hydroxypropoxy]quinoline,
5-[3-(4-(diphenylmethylene)piperidine-1-yl)-2-hydroxypropoxy]quinoline,
5-[3-(4-diphenylmethylpiperazine-1-yl)-2-hydroxypropoxy]isoquinoline,
5-[3-(4-(dibenzosuberane-5-yl)piperazine-1-yl)-2-hydroxypropoxy]isoquinoline,
5-[3-(4-diphenylmethylhomopiperazine-1-yl)-2-hydroxypropoxy]isoquinoline,
8-[3-(4-diphenylmethylpiperazine-1-yl)-2-hydroxylpropoxy]isoquinoline,
8-[3-(4-diphenylmethylpiperazine-1-yl)-2-hydroxylpropoxy]quinoline,
5-[3-(4-diphenylmethylpiperazine-1-yl)-2-hydroxylpropoxy]quinoxaline,
5-[3-(4-diphenylmethylpiperazine-1-yl)-2-hydroxylpropoxy]quinazoline,
5-(3-[4-((4-pyridyl)phenylmethyl)piperazine-1-yl]-2-hydroxylpropoxy)quinoline,
2,4-dimethyl-5-[3-((α,α-diphenylacetyl)piperazine-1-yl)-2-hydroxylpropoxy]quinoline,
2-trifluoromethyl-4-methyl-5-[3-(4-(dibenzosuberane-5-yl)piperazine-1-yl)-2-hydroxypropoxy]quinoline,
2-trifluoromethyl-4-methyl-5-[3-(4-(α,α-diphenylacetyl)-piperazine-1-yl)-2-hydroxypropoxy]quinoline,
2-trifluoromethyl-4-methyl-5-[3-(4-diphenylmethylpiperazine-1-yl)-2-hydroxypropoxy]quinoline,
5-(3-[4-(bis(4-fluorophenyl)methyl)piperazine-1-yl]-2-hydroxypropoxy)quinoline,
5-(3-[4-((4-chlorophenyl)-phenylmethyl)piperazine-1-yl]-2-hydroxypropoxy)quinoline,
5-(3-[4-(bis(4-methoxyphenyl)methyl)piperazine-1-yl]-2-hydroxypropoxy)quinoline,
5-[3-(4-(iminodibenzyl-5-carbonyl)piperazine-1-yl)-2-hydroxypropoxy]quinoline,
2,4-dimethyl-5-[3-(4-(iminodibenzyl-5-carbonyl)piperazine-1-yl)-2-hydroxypropoxy]quinoline,
5-[3-(N'-(dibenzosuberane-5-yl)ethylenediamino)-2-hydroxypropoxy]quinoline,
5-[3-(N,N'-dimethyl-N'-(dibenzosuberane-5-yl)ethylenediamino)-2-hydroxypropoxy]quinoline,
2-methylthio-5-[3-(4-(dibenzosuberane-5-yl)piperazine-1-yl)-2-hydroxypropoxy]quinoline,
2-methylthio-5-[3-(4-(α,α-diphenylacetyl)piperazine-1-yl)-2-hydroxypropoxy]quinoline,
2,4-dimethyl-5-[3-(N,N'-dimethyl-N'-(dibenzosuberane-5-yl)ethylenediamino)-2-hydroxypropoxy]quinoline,
2,4-dimethyl-5-[3-(4-diphenylmethylenepiperidine-1-yl)-2-hydroxypropoxy]quinoline,
5-[3-(10,11-dihydro-N-methyl-5 H-dibenzo[a,d]-cycloheptene-Δ$^5$,γ-propylamino)-2-hydroxypropoxy]quinoline,
5-[3-(3,3-diphenylpropylamino)-2-hydroxypropoxy]quinoline,
5-[3-(2,2-diphenylethylamino)-2-hydroxypropoxy]quinoline,
2-methylsulfonyl-5-[3-(4-(dibenzosuberane-5-yl)piperazine-1-yl)-2-hydroxypropoxy]quinoline,
5-[3-(4-(xanthene-9-yl)piperazine-1-yl)-2-hydroxypropoxy]quinoline, 5-[3-(N-methyl-3-(5-iminobenzyl)propylamino)-2-hydroxypropoxy]quinoline, 5-[3-(4-diphenylmethylpiperazine-1-yl)-2-hydroxy-propylthio]quinoline, and 5-[3-(4-(dibenzosuberane-5-yl)piperazine-1-yl)-2-hydroxypropylthio]quinoline.

Salts of the compounds according to the present invention include salts of inorganic acids such as hydrochloric acid and sulfuric acid as well as organic salts such as acetic acid, oxalic acid, maleic acid and tartaric acid. Compounds of the present invention have an asymmetic carbon atom in their structure, and therefore optical isomers exist. All of these optical isomers are regarded as within the present invention. The compounds of the present invention are prepared as follows: First synthetic method: A heterocyclic compound represented by the following formula is reacted with a halide such as epichlorohydrin or epibromohydrin in the presence of a base in a solvent at an appropriate temperature in order to form the corresponding epoxy compound. The above-mentiened base is an inorganic base such as sodium hydroxide, sodium hydride, potassium t-butoxide or sodium carbonate, or an organic base such as triethylamine, pyridine or DBU. The suitable solvent is an aqueous solvent or an organic solvent such as an alcohol, acetone, THF and DMF, and the reaction temperature is preferably in the range of 0° to 100° C.

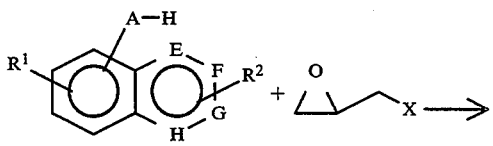

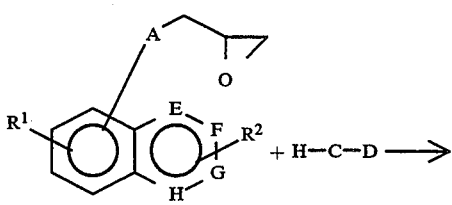

where $R^1$, $R^2$, A, E, F, G and H are as defined above, and X is a halogen atom.

Afterward, the synthesized epoxy compound is thermally reacted with a corresponding amine derivative in a solvent in order to obtain the compound having the general formula (I) wherein B is —CH$_2$CH(OH)CH$_2$— of the present invention.

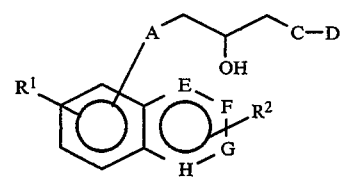

where $R^1$, $R^2$, A, E, F, G and H are as defined above.

As used above, "thermally" means in the temperature range of from room temperature to a boiling point of the used solvent. The solvent is an organic solvent such as an alcohol, acetone, chloroform or DMF.

A second method of synthesizing the compounds of the present invention is as follows: A halide such as epichlorohydrin or epibromohydrin is reacted with a corresponding amine derivative thermally or in the presence of a base in a solvent in order to form the corresponding epoxy compound and hydroxyhalogen compound.

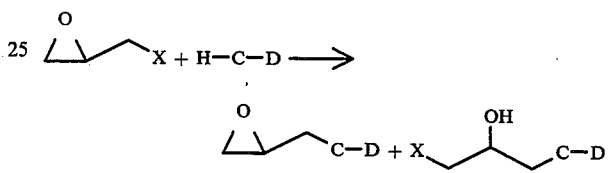

where X is a halogen, and C and D are as defined above.

Afterward, a heterocyclic compound represented by the following formula is reacted with the above synthesized epoxy compound or hydroxyhalogen compound thermally or in the presence of a base or acid in a solvent in order to obtain the compound having the general formula (I) wherein B is —CH$_2$CH(OH)CH$_2$— of the present invention.

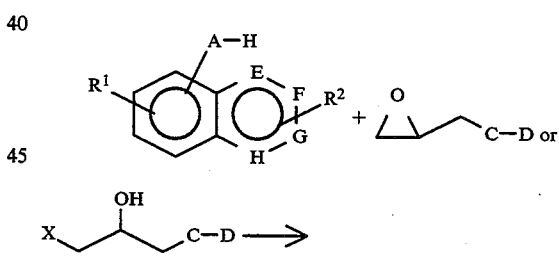

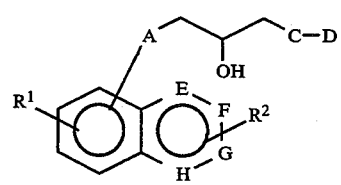

where $R^1$, $R^2$, A, C, D, E, F, G and H are as defined above, and X is a halogen.

The above-mentioned base is an inorganic base such as sodium hydroxide, sodium hydride, potassium t-butoxide or potassium carbonate, or an organic base such as triethylamine, pyridine or DBU.

The above-mentioned acid is an organic acid such as tosyl or camphorsulfonic acid, an inorganic acid such as hydrochloric acid or sulfuric acid, or a Lewis acid such as titanium tetrachloride, tin tetrachloride or trimethylsilyltrifluoromethanesulfonic acid.

The solvent used is an organic solvent such as methylene chloride, acetone, an alcohol, tetrahydrofuran or dimethylformamide. The term "thermally" means "in the temperature range of from room temperature to a boiling point of the solvent".

A third method of synthesizing the compounds of the present invention is as follows: A heterocyclic compound represented by the following formula is reacted with a dihalogenoalkyl material such as 1,2-dibromoethane, 1,3-dibromopropane, 1,3 =dichloropropane or 1,4-dibromobutane in the presence of a base in a solvent in order to form the corresponding halogenoalkyl compound.

The above-mentioned base is an inorganic salt such as sodium hydroxide, sodium hydride, potassium t-butoxide or sodium carbonate, or an organic base such as triethylamine, pyridine or DBU. The solvent used is an aqueous solvent or an organic solvent such as an alcohol, acetone, THF or DMF, and the reaction temperature is in the range of from room temperature to a boiling point of the used solvent.

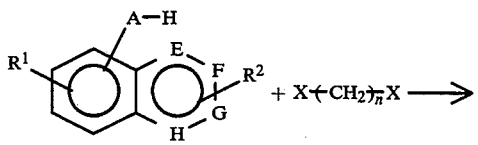

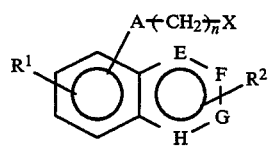

where $R^1$, $R^2$, A, E, F, G and H are as defined above, and X is a halogen atom.

Afterward, the synthesized halogenoalkyl compound is reacted with the corresponding amine derivative theremally in a solvent, thereby obtaining a compound having the general formula (I) wherein B is —$(CH_2)_n$— of the present invention.

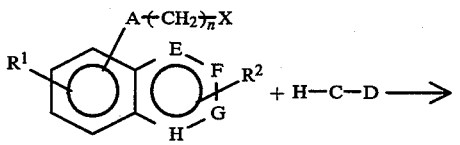

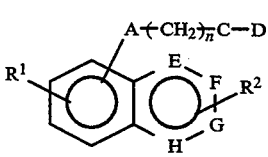

where $R^1$, $R^2$, A, C, D, E, F, G and H are as defined above, and X is a halogen atom.

The above-mentioned "thermally" means in the temperature range of from room temperature to a boiling point of the used solvent. The solvent used is an organic solvent such as an alcohol, acetone, chloroform or DMF.

A fouth method of synthesizing compounds of the present invention is as follows: A heterocyclic compound represented by the following formula is reacted with an acid halide such as 3-chloropropionyl chloride, or an acid anhydride theremally or in the presence of a base in a solvent, thereby forming the corresponding halide.

The above-mentioned "thermally" means in the temperature range of from room temperature to a boiling point of the used solvent.

The above-mentioned base is an inorganic base such as sodium hydroxide, sodium hydride or potassium t-butoxide, or an organic base such as triethylamine, pyridine or DBU. The solvent used is an organic solvent such as methylene chloride, chloroform or toluene.

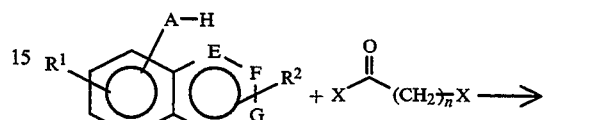

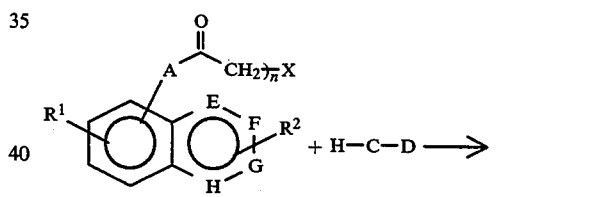

where $R^1$, $R^2$, A, E, F, G, H and X are as defined above.

Afterward, the synthesized halide is thermally reacted with a corresponding amine derivative in a solvent in order to obtain a compound having the general formula (I) wherein B is —$CO(CH_2)_n$— of the present invention.

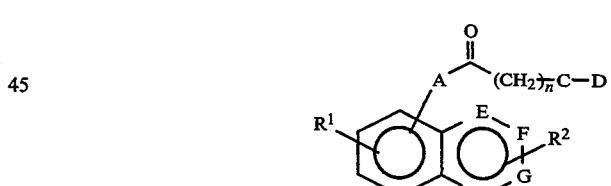

where $R^1$, $R^2$, A, C, D, E, F, G, H and X are as defined above.

The above-mentioned "thermally" means in the temperature range of from room temperature to a boiling point of the used solvent. The solvent used is an organic solvent such as acetone, chloroform, an alcohol or DMF.

A fifth method of synthesizing compounds of the present invention is as follows: The hydroxyl group of the compound which has been obtained by the first or second method is reacted with a corresponding acyl chloride or the like, thereby preparing a compound having the general formula (I) wherein B is —$CH_2CH(OCOR^3)CH_2$—. Alternatively, the above compound is reacted with p-toluenesulfonyl chloride or methanesulfonyl chloride, and the resultant product is then reacted with an alkoxide of an alkaline metal or an alkylamine to perform a substitutional reaction, thereby preparing the compound of the general formula (I) wherein B is —CH$_2$CH(R$^4$)CH$_2$—.

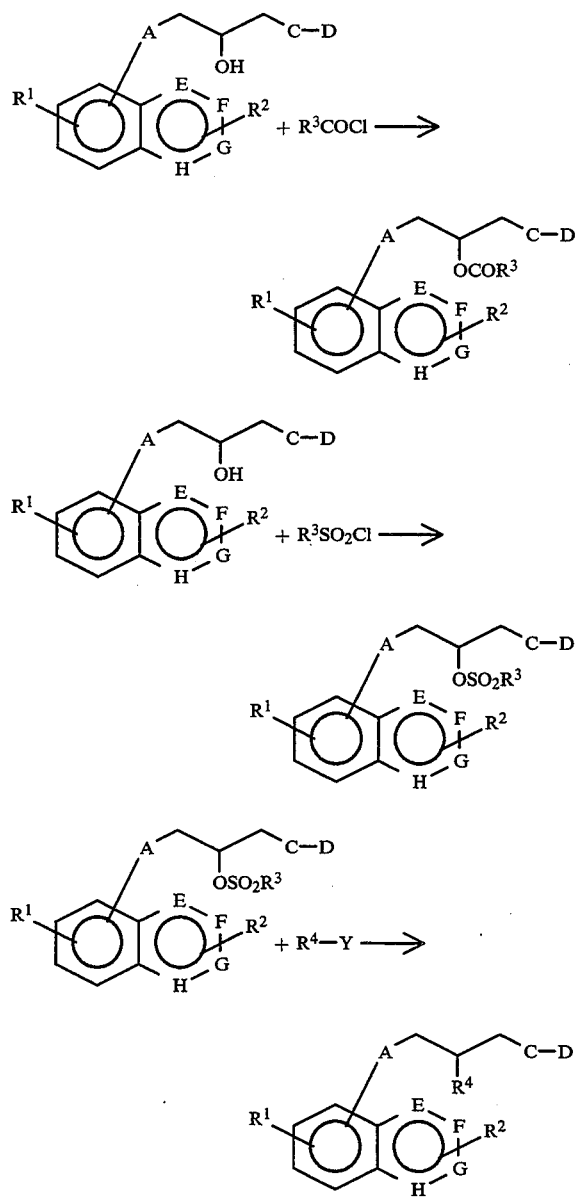

wherein R$^1$, R$^2$, A, C, D, E, F, G and H are as defined above, R$^3$ is a hydrogen atom or a lower alkyl group, R$^4$ is a lower alkoxy group, lower acyloxy group or lower alkylamino group, and Y is an alkaline metal or hydrogen atom.

The present invention will now be described in detail wtih reference to the following examples, but the scope of the present invention is not be limited to these examples.

The relative ability of the compounds of the present invention to potentfate the effect of anticancer drugs on drug-resistant cancer was assessed by measuring the incorporation of anticancer drugs into cells and by enforcement of therapeutic activity of anticancer drugs, using an adriamycin-resistant strain 2780 AD of human ovarian cancer cells or an adriamycin-resistant strain K562/ADM of human myeloleukemia cells. Adriamycin is an anticancer drug.

The compounds according to the present invention manifest remarkable reinforcement activity in the incorporation of anticancer drugs and reinforcement activity in therapeutic effect of anticancer drugs, which will be explained in detail in the following Examples.

Anticancer drugs suitable for use in combination with the compounds or the salts thereof according to the present invention are not specifically limited: those preferably used are, for example, non-antimetabolites such as anthracycline group antibiotics, e.g. adriamycin, daunomycin or acrasinomycin A, actinomycin group antibiotics, actinomycin C or actinomycin D, chromomycin group antibiotics, e.g. mithramycin or toyomycin, vincalkaloids, e.g. vincristine or vinblastine, meitansins, podophyllotoxin derivatives, e.g. VP16-213, homoharintonin, angwindin, bruceantin, neocarcinostatin, anthramycin, mitomycin C and cisplatin derivatives.

The compounds and the salts thereof according to the present invention can be administered independently with before or after the administration of anticancer drugs or in combination with anticancer drugs in the same delivered dosage unit, The compounds and their salts according to the present invention can be adminis- te.red as preparations suited to various means of administration independently with various anticancer drugs or, alternatively, can be administered as preparations mixed with anticancer drugs. Nodes of administration are naturally different depending on the symptom(s) of patients to be treated. Physical form of anticancer drugs, etc. Amounts in the range between 1 and 1,000 mg/day for an adult in a single or divided doses can be used orally in forms such as tablets, granules, powders, suspensions, capsules or syrups, or as patenfetal drugs such as injections, depositories or isotonic fluids for infusion.

For example, when prepared in a tablet form, examples of absorbents to be used include crystallized cellulose and calcium silicate, and examples of excipients are corn starch, lactose, calcium phosphate and magnesium stearate among others. Furthermore, examples of injections to be used are in a form of suspension in water or aquous suspension with cotton seed oil, corn oil, peanut oil, olive oil, etc. or emulsion, for example, with compatible surfactants such as HCO-60. The anticancer drugs may be used as they are without modification.

The compounds according to the present invention strongly suppress the outflow of anticancer drugs from cancer cells and, moreover, are characterized by their low toxicity and extremely low incidence of side effects such as hypotonia.

The compounds according to the present invention are effective towards cancer cells, especially those less sensitive or resistant to anticancer drugs, and can thus provide new therapeutic opportunities for those patients afflicted with such cancers and tumors.

The present invention is further illustrated by the following examples.

EXAMPLE 1

5-[3-(4-Diphenylmethylpiperazine-1-yl)-2-hydroxypropoxy]quinoline (a) In 20 ml of dried DMF was dissolved 1 g of 5-hydroxyquinoline, and 0.28 g of sodium hydride (60% content) was then added thereto, followed by heating with stirring at 50° C. for 30 minutes. Afterward, 1.92 g of epichlorohydrin was further added to the reaction liquid and the latter was then heated with stirring at 90° C. for 3 hours, and the solvent was distilled off under reduced pressure. Water was then added to the residue, and the liquid was extracted with chloroform. The chloroform extract was then decolored and purified with active carbon, then was dried with anhydrous sodium sulfate, and was distilled off. The residue was then purified through a silica gel column chromatograph by the use of an effluent solvent of chloroform:methanol=100:1, so that 0.88 g of 5-(2,3-epoxypropoxy)quinoline was obtained in an oily state.

(b) In 20 ml of ethanol were dissolved 0.88 g of the above obtained epoxy compound and 1.1 g of N-diphenylmethylpiperazine, and the liquid was then heated under reflux for 3 hours. After reaction, ethanol was distilled off, and the residue was then purified through a silica gel column chromatograph, using chloroform:methanol=50:1 as an effluent solvent. Afterward, fractions containing the desired compound were combined. The solvent was then distilled off, and a small amount of ether was added to the residue for the purpose of crystallization. Afterward, the crystals were filtered and dried in order to obtain 1.5 g of 5-[3-(4-diphenylmethylpiperazine-1-yl)-2-hydroxypropoxy]-quinoline.

m.p.: 161°–163° C.

IR $\nu cm^{-1}$ (KBr): 3400 (br), 2790, 1580, 1265, 1092, 788

NMR $\delta$ppm (CDCl$_3$): 2.3–2.9 (m,10H), 3.55 (br,s,1H), 4.05–4.25 (m,4H), 6.82 (d,d,1H), 7.1–7.8 (m,13H), 8.54 (d,d,1H), 8.84 (d,d,1H)

EXAMPLE 2

5-[3-(4-(Dibenzosuberane-5-yl)piperazine-1-yl)-2-hydroxypropoxy]quinoline (a) With 80 ml of dioxane was mixed 11.3 g of anhydrous piperazine, and 5.0 g of 5-chlorobenzosuberane was then added thereto. Afterward, the reaction liquid was heated under reflux for 7 hours. After cooling, insoluble substances were removed by filtration, and the solvent was also distilled off. A small amount of petroleum ether was added to the residue for the purpose of crystallization, the crystals were collected by filtration and were then dried, thereby obtaining 5.1 g of N-(dibenzosuberane-5-yl)piperazine.

m.p.: 110°–111.5° C.

IR $\nu cm^{-1}$(KBr): 3420, 3250, 2920, 2800, 1630, 1490, 1450, 1330, 1140

(b) In 20 ml of ethanol were dissolved 0.88 g of the epoxy compound obtained in the step (a) of Example 1 and 1.2 g of N-(dibenzosuberane-5-yl)piperazine, and the liquid was then heated under reflux for 3 hours. After reaction, the solvent was distilled off, and the residue was then purified through a silica gel column chromatograph.

A solvent of chloroform:methanol=50:1 was used as an effluent solvent, so that 5-[3-(4-(dibenzosuberane-5-yl)-piperazine-1-yl)-2-hydroxypropoxy]quinoline which was the aimed compound was obtained in an amount of 1.4 g.

IR $\nu cm^{-1}$(KBr): 2900, 2800, 1620, 1590, 1570, 1450, 1260, 1140, 1100

NMR $\delta$ppm (CDCl$_3$): 2.1–3.0 (m,12H), 3.1–3.6 (br,s,1H), 3.7–4.4 (m,6H), 6.8 (d,1H), 6.9–7.9 (m,11H), 8.5 (d,1H), 8.8 (d,1H)

EXAMPLE 3

5-(3-[N-(2-(N-Diphenylmethyl-N-methylamino)ethyl)-N-methylamino]-2-hydroxypropoxy)quinoline (a) In 100 ml of dioxane were dissolved 25 g of N,N'-dimethylethylenediamine and 6 g of diphenylmethyl chloride, and the liquid was then heated under reflux for 4 hours. The solvent was distilled off, and water was then added to the residue, followed by extracting with chloroform.

The chloroform extract was then dried with anhydrous sodium sulfate, and the solvent was distilled off.

The residue was then purified through a silica gel column chromatograph by the use of a solvent of chloroform:methanol=25:1, thereby obtaining 4.6 g of N-diphenylmethyl-N,N'-dimethylethylenediamine in an oily state.

IR $\nu cm^{-1}$: 2960, 2860, 2800, 1600, 1500, 1460, 1030

NMR $\delta$ppm (CDCl$_3$): 1.8 (s,1H), 2.1 (s,3H), 2.35 (s,3H), 2.4–2.8 (m,4H), 4.35 (s,1H), 7.1–7.6 (m,10H)

(b) In 20 ml of ethanol were dissolved 1.06 g of the above obtained amine compound and the epoxy compound obtained in Example 1-(a), and the liquid was then heated under reflux for 3 hours. The solvent was then distilled off under reduced pressure, and the residue was purified through a silica gel column chromatograph by the use of an effluent of chlcroform:methanol=100:1, thereby obtaining 1.3 g of 5-(3-[N-(2-(N-diphenylmethyl-N-methylamino)ethyl)-N-methylamino]-2-hydroxypropoxy)quinoline.

IR $\nu cm^{-1}$: 2960, 2800, 1620, 1590, 1580, 1490, 1450, 1280

NMR $\delta$ppm (CDCl$_3$): 2.2 (s,3H), 2.3 (s,3H), 2.4–3.0 (m,3H), 3.9–4.25 (m,4H), 4.3 (s,1H), 6.9 (d,1H), 7.0–7.8 (m,13H), 8.5 (d,1H), 8.85 (d,1H)

EXAMPLE 4

5-[3-(4-Diphenylmethylhomopiperazine-1-yl)-2-hydroxypropoxy]quinoline

In 20 ml of ethanol were dissolved 0.88 g of the epoxy compound obtained in Example 1-(a) and 1.2 g of N-diphenylmethylhomopiperazine, and the liquid was then heated under reflux for 3 hours. After reaction, the solvent was distilled off, and the residue was then purified through a silica gel column chromatograph. A solvent of chloroform:methanol=50:1 was used as an effluent solvent, so that 5-[3-(4-diphenylmethylhomopiperazine-1-yl)-2-hydroxypropoxy]quinoline which was intended therein was obtained in an amount of 1.6 g.

IR $\nu cm^{-1}$(KBr): 3040, 3000, 2920, 2820, 1610, 1580, 1570, 1460, 1260, 1170

NMR $\delta$ppm (CDCl$_3$): 1.8 (t,2H), 2.4–3.2 (m,10H), 3.65 (s,1H), 4.15 (s,3H), 4.6 (s,1H), 6.8 (d,1H), 7.0–7.9 (m,13H), 8.5 (d,1H), 8.8 (d,1H)

EXAMPLE 5

2,4-Dimethyl-5-[3-(4-diphenylmethylpiperazine-1-yl)-2-hydroxypropoxy]quinoline (a) With 5.0 g of acetylacetone was mixed 2.8 g of 3-amino-2-cyclohexenone, and the liquid was then heated with stirring at 70° C. for 1 hour. The heating was further continued at a temperature of 160 to 170° C. for 9 hours.

Excess acetylacetone and water were distilled off under reduced pressure, and the residue was then purified through a silica gel column chrometograph by the use of an effluent of chloroform:methanol=50:1, thereby obtaining 1.85 g of 2,4-dimethyl-5,6,7,8-tetrahydro-5-oxoquinoline.

m.p.: 54°–57° C.

(b) In 15 ml of diethylene glycol butylether acetate were dissolved 1.6 g of the above synthesized tetrahydroquinoline compound and 0.2 g of 10% Pd-C, and the liquid was then heated with stirring at 200° C. for 6 hours under a nitogen gas stream.

After cooling, the deposited crystals were separated from Pd-C by filtration, and the solvent was distilled off and the solvent-free filtrate was then purified through a silica gel column chromatograph to obtain the desired product. Furthermore, the deposited crystals were dissolved in methanol, then filtered to remove Pd-C therefrom, and evaporated to dryness under reduced pressure, thereby obtaining the desired compound, 2,4-dimethyl-5-hydroxyquinoline.

Total yield: 0.82 g m.p.: 222°–224° C.

NMR δppm (DMSO-d$_6$): 2.50 (s,3H), 2.82 (s,3H), 6.7–7.1 (m,2H), 7.20–7.50 (m,2H), 10.0 (s,1H)

(c) Following the same procedure as in Example 1-(a), 0.72 g of the above synthesized hydroxyquinoline compound and epichlorohydrin were subjected to reaction and treatment in order to form an epoxy compound. The latter was further reacted and treated with the diphenylpiperazine compound in accordance with the same procedure as in Example 1-(b), thereby obtaining 1.13 g of 2,4-dimethyl-5-[3-(4-diphenylmethylpiperazine-1-yl)-2-hydroxypropoxy]quinoline.

IR $\nu$cm$^{-1}$(KBr): 3400, 2800, 1600, 1450, 1260, 1050

NMR δppm (CDCl$_3$): 2.5–2.85 (m,16H), 3.65 (br,s,1H), 4.0–4.3 (m,4H), 6.75 (d,1H), 7.0 (s,1H), 7.15–7.6 (m,12H)

EXAMPLE 6

5-[3-(4-(6,11-Dihydrodibenzo[b,e]oxepine-11-yl)piperazine-1-yl)-2-hydroxypropoxy]quinoline (a) In 90 ml of dried ether was dissolved 4.05 g of 6H-dibenzo[b,e]oxepine-11-one, and the liquid was then added dropwise, while being cooled with ice, to a solution in which LiAlH$_4$ was dispersed in 70 ml of dried ether.

The liquid was heated under reflux for 4.5 hours and was then cooled, and a saturated aqueous Glauber's salt solution was added thereto.

The liquid was filtered to remove insoluble substances therefrom, followed by drying. The solvent was then distilled off, and the residue was purified through a silica gel column chromatograph by the use of an effluent solvent of chloroform:methanol=100:1 in order to obtain 4.0 g of 11-hydroxy-6,11-dihydrodibenzo[b,e]oxepine.

IR $\nu$cm$^{-1}$(KBr): 3260, 1600, 1570, 1480, 1440, 1280, 1250

NMR δppm (CDCl$_3$): 1.55 (s,1H), 4.75–4.95 (m,1H), 5.3 (s,1H), 5.8–6.3 (m,1H), 6.5–7.6 (m,8H)

(b) In 70 ml of dried methylene chloride was dissolved 3.6 g of the above obtained 11-hydroxydibenz[b,e]oxepine, and 3.0 g of thionyl chloride was then added dropwise thereto under cooling with ice. After stirring at room temperature for 1 hour, the excessive solvent and thionyl chloride were distilled off under reduced pressure.

Furthermore, the residue was dissolved in 40 ml of methylene chloride, and the liquid was then added to a solution in which 8.8 g of anhydrous piperazine was dissolved in 90 ml of methylene chloride, followed by stirring at room temperature for 1 hour.

Insoluble substances were removed therefrom by filtration, and the filtrate was washed with water and was then dried.

After the solvent was distilled off, the liquid was purified with a silica gel column chromatograph, using an effluent solvent of chloroform:methanol=20:1, in order to obtain 3.2 g of 11-piperazino-6,11-dihydrodibenzo[b,e]oxepine.

NMR δppm (CDCl$_3$): 2.1 (s,1H), 2.2–3.0 (m,8H), 3.8 (s,1H), 4.6 (d,]H), 6.7 (s,1H), 6.8–7.3 (m,8H) (c) Following the same procedure as in Example 1-(b), 2.5 g of the above synthsized dizenzooxepine compound and 1.1 g of the epoxy compound synthesized in Example 1-(a) were subjected to reaction and treatment, thereby obtaining 2.6 g of 5-[3-(4-(6,11-dihydrodibenzo[b,e]oxepine-11-yl)piperazine-1-yl)-2-hydroxypropoxy]quinoline.

IR $\nu$cm$^{-1}$(KBr): 3400, 2930, 2800, 1615, 1590, 1570, 1480, 1450, 1270

NMR δppm (CDCl$_3$): 2.1–3.0 (m,10H), 3.9 (s,1H), 4.05–4.3 (m,3H), 4.7 (d,1H), 6.8 (t,4H), 7.0–7.4 (m,8H), 7.55 (t,1H), 7.7 (d,1H), 8.55 (d,1H), 8.55 (d,1H)

EXAMPLE 7

5-[3-(4-(Diphenyl-hydroxymethyl)piperidine-1-yl)-2-hydroxypropoxy]quinoline

Reaction and treatment were carried out using 0.4 g of the epoxy compound synthesized in Example 1-(a) and 0.6 g of -(diphenyl-hydroxymethyl)piperidine in accordance with the same procedure as in Example 1-(b), in order to obtain 0.75 g of 5-[3-(4-(diphenyl-hydroxymethyl)piperidine-1-yl)-2-hydroxypropoxy]-quinoline.

IR $\nu$cm$^{-1}$(KBr): 3380, 2925, 1610, 1580, 1568, 1265 1095, 790, 740, 695

NMR δppm (CDCl$_3$): 1.55 (m,4H), 2.09 (m,1H), 2.3–2.5 (m,2H), 2.5–2.7 (m,2H), 2.95 (m,1H), 3.09 (m,1H), 3.6 (br,2H), 4.0–4.25 (m,3H), 6.80 (d.1H), 7.15 (m,2H), 7.2–7.35 (m,5H), 7.4–7.6 (m,5H), 7.66 (d. 1H), 8.53 (dd,1H), 8.81 (dd,1H)

EXAMPLE 8

5-[3-(4-(2,2-Diphenylacetyl)piperazine-1-yl)-2-hydroxypropoxy]-2-methoxyquinoline (a) Reaction and treatment were carried out using 1.6 g of 5-hydroxy-2-methoxyquinoline in accordance with the same procedure as in Example 1-(a), in order to obtain 5-(2,3-epoxypropoxy)-2-methoxyquinoline.

NMR δppm (CDCl$_3$): 2.82 (dd,1H), 2.95 (t,1H), 3.4–3.5 (m,1H), 4.0–4.2 (m,1H), 4.06 (s,3H), 4.38 (dd,1H), 6.71 (dd,1H), 6.86 (d,1H), 7.4–7.55 (m,2H), 8.42 (d,1H)

(b) Reaction and treatment were carried out using 0.7 g of the above synthesized epoxy compound and 1.0 g of N-(2,2-diphenylacetyl) piperazine in accordance with the same procedure as in Example 1-(b), in order to obtain 1.39 g of 5-[3-(4-(2,2-diphenylacetyl)piperazine-1-yl)-2-hydroxypropoxy]-2-methoxyquinoline.

IR $\nu$cm$^{-1}$(KBr): 1630, 1610, 1590, 1570, 1430, 1395, 1310, 1240

NMR δppm (CDCl$_3$): 2.2–2.8 (m,6H), 3.4–3.6 (m,2H), 3.6–3.9 (m,2H), 3.9–4.3 (m,6H), 5.19 (s,1H), 6.6–6.75 (m,1H), 6.85 (d,1H), 7.0–7.6 (m,14H), 8.34 (d,1H)

EXAMPLE 9

5-[3-(4-(Dibenzosuberane-5-yl)piperazine-1-yl)-2-hydroxypropoxy]-2-methoxyquinoline Reaction and treatment were carried out using 0.7 g of the epoxy compound synthesized in Example 8-(a) and 0.92 g of the dibenzosuberanylpiperazine compound synthesized in Example 2-(a), in order to obtain 1.22 g of the desired compound.

IR $\nu cm^{-1}$ (KBr): 3040, 3000, 2920, 2800, 1610, 1595, 1570, 1430, 1395, 1310, 1200

NMR δppm (CDCl$_3$): 2.2–2.9 (m,12H), 3.9–4.2 (m,6H), 4.05 (s,3H), 6.71 (dd,1H), 6.84 (d,1H), 7.0–7.3 (m,8H), 7.4–7.52 (m,2H), 8.37 (d,1H)

EXAMPLE 10

5-(3-[N-(2-(N-Diphenylmethyl-N-ethylamino)ethyl)-N-ethylamino]-2-hydroxypropoxy)quinoline (a) Reaction and treatment were carried out using 21 g of N,N'-diethylethylenediamine and 7.3 g of diphenylmethyl chloride in accordance with the same procedure as in Example 3-(a), in order to obtain 4.2 g of N-diphenylmethyl-N,N'-diethylethylenediamine.

NMR δppm (CDCl$_3$): 0.9–1.4 (m,6H), 2.4–3.2 (m,8H), 4.8 (s,1H), 7.1–7.8 (m,10H)

(b) Reaction and treatment were carried out using 1.52 g of the above synthesized diamine compound and 1.08 g of the epoxy compound synthesized in Example 1-(a) in accordance with the same procedure as in Example 1-(b), in order to obtain 0.5 g of 5-(3-[N-(2-(N-diphenylmethyl-N-ethylamino)ethyl)-N-ethylamino]-2-hydroxypropoxy)quinoline.

IR $\nu cm^{-1}$(KBr): 3400, 1630, 1590, 1450, 1410, 1280, 1100

NMR δppm (CDCl$_3$): 1.0 (m,6H), 2.3–2.9 (m,10H), 3.95–4.2 (m,4H), 6.85 (d,1H), 7.0–7.85 (m,11H), 8.55 (d,1H), 8.9 (d,1H)

EXAMPLE 11

5-[3-(4-(2,3,3',4'-Tetramethoxydiphenylmethyl)piperazine-1-yl)-2-hydroxypropoxy]quinoline (a) Following the same procedure as in Example 6-(b), reaction and treatment were carried out using 3.45 g of 2,3,3',4'-tetramethoxybenzohydrol in order to obtain 3.1 g of N-(2,3,3',4'-tetramethoxydiphenylmethyl)-piperazine.

NMR δppm (CDCl$_3$): 1.9 (s,1H), 2.35 (s,4H), 2.85 (t,4H), 3.8 (s,12H), 4.7 (s,1H), 6.75 (m,2H), 7.0 (m,3H), 7.25 (s,1H)

(b) Following the same procedure as in Example 1-(b), reaction and treatment were carrried out using 3.1 g of the above synthesized piperazine derivative and 0.86 g of the epoxy compound synthesized in Example 1-(a), in order to obtain 1.82 g of 5-[3-(4-(2,3,3',4'-tetramethoxydiphenylmethyl)piperazine-1-yl)-2-hydroxypropoxy]quinoline.

IR $\nu cm^{-1}$ (KBr): 3400, 2920, 1640, 1595, 1520, 1480, 1420, 1280

NMR δppm (CDCl$_3$): 1.8–2.3 (m, 1H), 2.3–2.9 (m,10H), 3.5–4.0 (s,12H), 4.05–4.4 (m,3H), 4.7 (s,1H), 6.75 (q,2H), 6.85 (d,1H), 6.95–7.1 (m,3H), 7.25 (s,1H), 7.35 (q,1H), 7.55 (t,1H), 7.7 (d,1H), 8.55 (d,1H), 8.9 (q,1H)

EXAMPLE 12

3-Ethyl-5-[3-(4-diphenylmethylpiperazine-1-yl)-2-hydroxypropoxy]quinoline

In 10 ml of DMF was dissolved 750 mg of 3-ethyl-5-hydroxyquinoline, and 180 mg of 60% sodium hydride was then added thereto. The solution was stirred at 50° C. for 30 minutes, and 1.25 g of epichlorohydrin was then added thereto, followed by stirring at 90° C. for 3 hours. Afterward, the solvent was distilled off, and the residue was dissolved in chloroform and was then washed with water. The chloroform layer was dried and concentrated, and this residue was dissolved in 10 ml of ethanol. Furthermore, 750 mg of N-diphenylmethylpiperazine was added thereto, and the liquid was then heated under reflux for 3 hours. The solvent was then distilled off, and the residue was purified through a silica gel column chromatograph by the use of an effluent solvent of chloroform:methanol=50:1, thereby obtaining 800 mg of 3-ethyl-5-[3-(4-diphenylmethylpiperazine-1-yl)-2-hydroxypropoxy]quinoline.

IR $\nu cm^{-1}$(KBr): 3450, 2805, 1600, 1578, 1450, 1262, 1090, 742, 705

NMR δppm (CDCl$_3$): 1.32 (t,3H), 2.3–2.85 (m,12H), 4.0–4.25 (m,4H), 6.80 (d,1H), 7.1–7.28 (m,6H), 7.37–7.5 (m,5H), 7.64 (d,1H), 8.28 (d,1H), 8.73 (d,1H)

EXAMPLE 13

5-[3-(4-(Diphenylmethylene)piperidine-1-yl)-2-hydroxypropoxy]quinoline

Following the same procedure as in Example 1-(b), reaction and treatment were carried out using 1.25 g of 4-(diphenylmethylene)piperidine, thereby obtaining 0.96 g of the desired compound.

NMR δppm (CDCl$_3$): 2.3–3.0 (m,10H), 4.1–4.4 (m,3H), 6.87 (d,1H), 7.0–7.5 (m,11H), 7.5–7.8 (m,2H), 8.5–8.75 (m,1H), 8.75–9.0 (m,1H)

EXAMPLE 14

5-[3-(4-(Diphenylmethyl)piperidine-1-yl)-2-hydroxypropoxy]quinoline

Following the same procedure as in Example 1-(b), reaction and treatment were carried out using 1.09 g of 4-(diphenylmethyl)piperidine, thereby obtaining 0.14 g of the desired compound.

NMR δppm (CDCl$_3$ +DMSO-d$_6$): 1.6–1.9 (m,4H), 2.3–2.5 (m,1H), 2.5–2.7 (m,3H),-2.7–3.0 (m,1H), 3.0–3.3 (m,1H), 3.3–3.7 (m,3H), 4.1–4.3 (m,2H), 4.55–4.75 (m,1H), 6.83–6.94 (m,1H), 7.68–7.70 (m,13H), 8.6–8.7 (m,1H), 8.84–8.92 (m,1H)

EXAMPLE 15

5-[2-Hydroxy-3-(4-(phenyl-2-pyridylmethyl)piperazine-1-yl)propoxy]quinoline

Following the same procedure as in Example 1-(b), reaction and treatment were carried out using 0.93 g of N-(phenyl-2-pyridylmethyl)piperazine to obtain 1.22 g of the desired compound.

NMR δppm (CDCl$_3$): 1.57 (s,1H), 2.3–2.9 (m,10H), 4.05–4.30 (m,3H), 4.45 (s,1H), 6.87 (d,1H), 7.05–7.72 (m,12H), 8.52 (d,1H), 8.58 (d,1H), 8.90 (dd,1H)

EXAMPLE 16

5-[3-(4-(2,2-Diphenylacetyl)piperazine-1-yl)-2-hydroxypropoxy]quinoline

Following the same procedure as in Example 1-(b), reaction and treatment were carried out using 0.85 g of the epoxy compound synthesized in Example 1-(a) and 1.12 g of N-(2,2-diphenylacetyl)piperazine to obtain ].2 g of the desired compound.

NMR δppm (CDCl$_3$): 2.7–2.3 (m,1H), 2.3–2.75 (m,5H), 3.3–3.6 (m,3H), 3.6–3.8 (m,2H), 4.05–4.25 (m,3H), 5.18 (s,1H), 6.83 (d,1H), 7.1–7.45 (m,11H), 7.57 (t,1H), 7.69 (d,1H), 8.4–8.55 (m,1H)

EXAMPLE 17

5-[3-(4-(2,2-Diphenylethyl)piperazine-1-yl)-2-hydroxypropoxy]quinoline

Following the same procedure as in Example 1-(b), reaction and treatment were carried out using 0.85 g of the epoxy compound synthesized in Example 1-(a) and 1.07 g of N-(2,2-diphenylethyl)piperazine to obtain 1.2 g of the desired compound.

NMR δppm (CDCl$_3$): 2.3–2.75 (m,10H), 2.97 (d,2H), 4.0–4.25 (m,4H), 6.85 (d,1H), 7.70–7.70 (m,13H), 8.45–8.55 (m,1H), 8.80–8.92 (m,1H)

EXAMPLE 18

5-[3-(4-(5-Dibenzosuberanyl)piperazine-1-yl)-2-hydroxypropoxy]-2-chloroquinoline (a) Following the same procedure as in Example 1-(a), reaction and treatment were carried out using 0.8 g of 2-chloro-5-hydroxyquinoline to obtain 0.62 g of 2-chloro-5-(2,3-epoxypropoxy)quinoline.

IR νcm$^{-1}$(KBr): 3040, 2980, 2820, 1610, 1580, 1490, 1460, 1395, 1370, 1290, 1260, 1200, 1170, 1140, 1130, 1075, 1060, 900, 860, 820, 790, 740

(b) Following the same procedure as in Example 1-(b), reaction and treatment were carried out using 0.32 g of the above sinthesized epoxy compound.and 0.37 g of N-(dibenzosuberanyl)piperazine synthesized in Example 2-(a), in order to obtain 0.63 g of 5-[3-(4-(dibenzosuberanyl)piperazine-1-yl)-2-hydroxypropoxy]-2-chloroquinoline.

NMR δppm (CDCl$_3$): 2.15–2.9 (m,12H), 3.9–4.25 (m,6H), 6.75–6.95 (m,1H), 6.95–7.40 (m,9H), 7.58 (d,1H9, 8.47 (d,1H)

EXAMPLE 19

5-[3-(4-(Diphenyl-hydroxymethyl)piperidine-1-yl)-2-hydroxypropoxy]-2-chloroquinoline Following the same procedure as in Example 1-(b), reaction and treatment were carried out using 0.31 g of the epoxy compound synthesized in Example 18-(a) and 0.35 g of 4-(diphenyl-hydroxymethyl)piperidine to obtain 0.52 g of the desired compound.

NMR δppm (CDCl$_3$): 1.35–1.6 (m,4H), 1.95–2.7 (m,6H), 2.8–3.0 (m,1H), 3.0–3.2 (m,1H), 4.0–4.25 (m,3H), 6.8–6.9 (m,1H), 7.1–7.65 (m,13H), 8.48 (d,1H)

EXAMPLE 20

5-[3-(4-(5-Dibenzosuberenyl)piperazine-1-yl)-2-hydroxypropoxy]quinoline

Following the same procedure as in Example 1-(b), reaction and treatment were carried out using 0.4 g of the epoxy compound synthesized in Example 1-(a) and 0.6 g of N-(dibenzosuberenyl)piperazine to obtain 0.85 g of the desired compound.

NMR δppm (CDCl$_3$): 1.9–2.7 (m,10H), 4.0–4.25 (m,3H), 4.29 (s,1H), 6.82 (d,1H), 6.96 (s,2H), 7.15–7.80 (m,11H), 8.40–8.50 (m,1H), 8.80–8.90 (m,1H)

EXAMPLE 21

2,4-Dimethyl-5-[3-(4-(6,11-dihydrodibenzo[b,e]oxepine-11-yl)piperazine-1-yl)-2-hydroxypropoxy]quinoline Following the same procedure as in Example 5-(c), reaction and treatment were carried out using 0.8 g of 2,4-dimethyl-5-hydroxyqunoline prepared in Example 5-(b) and 1.04 g of 11-piperazino-6,11-dihydro-dibenzo[b,e]oxepine prepared in Example 6-(b), in order to obtain 1.6 g of the desired compound.

IR νcm$^{-1}$(KBr): 3400, 1630, 1594, 1440, 1380, 1260

NMR δppm (CDCl$_3$): 2.25–2.6 (m,10H), 2.6 (s,3H), 2.85 (s,3H), 3.9 (s,1H), 4.05–4.25 (m,3H), 4.7 (d,1H), 6.8 (m,4H), 6.95 (s,1H), 7.05–7.35 (m,6H), 7.5 (t,1H), 7.6 (d,1H)

EXAMPLE 22

5-[3-(4-(Dibenzosuberane-5-yl)piperazine-1-yl)-2-hydroxypropoxy]-2,4-dimethylquinoline Following the same procedure as in Example 5-(c), reaction and treatment were carried out using 0.8 g of 2,4-dimethyl-5-hyroxyquilne synthesized in Example 5-(b) and 1.04 g of dibenzosuberanylpiperazine synthesized in Example 2-(a), in order to obtain 1.6 g of the desired compound.

NMR δppm (CDCl$_3$): 2.2–2.9 (m,12H), 2.62 (s,3H), 2.83 (s,3H), 3.9–4.25 (m,6H), 6.75 (d,1H), 6.95–7.25 (m,9H), 7.48 (t,1H), 7.59 (d,1H)

EXAMPLE 23

5-[3-(4-Diphenylmethylpiperazine-1-yl)-2-hydroxypropoxy]-6-methylguinoline (a) In 20 ml of a 80% aqueous sulfuric acid solution were dissolved 3.48 g of 3-amino-6-methylphenol, 5.5 ml of glycerol and 7 g of sodium m-nitrobenzene sulfonate, and the liquid was then heated with stirring at 150° C. for 1 hour.

After cooling, the liquid was neutralized with an aqueous sodium hydroxide solution to a pH of 8 to 9.

The resulting aqueous layer was removed therefrom by filtration, and the residue was then dissolved in methanol and insoluble substances were afterward filtered off.

The methanol solution was concentrated and then purified through a silica gel column chromatograph by the use of an effluent solvent of chloroform:methanol=25:1, thereby obtaining 0.17 g of 5-hydroxy-6-methylquinoline and 1.6 g of 7-hydroxy-6-methylquinoline.

5-Hydroxy-6-methyl-quinoline: IR νcm$^{-1}$ (KBr): 1578, 1255, 1178, 1082, 915, 800

NMR δppm (CMSO-d$_6$): 2.4 (s,3H), 7.42 (dd,1H), 7.5 (s,1H), 8.62 (dd,1H), 8.78 (dd,1H), 9.3 (br,1H)

7-Hydroxy -6-methylquinoline:

NMR δppm (CMSO-d$_6$): 2.38 (s,3H), 7.31 (dd,1H), 7.4 (s,1H), 7.7 (s,1H), 8.20 (dd,1H), 8.72 (dd,1H)

(b) In 50 ml of acetone were dissolved 5.04 g of diphenylmethylpiperazine and 5.5 g of epichlorohydrin, and 4.2 ml of triethylamine was then added thereto.

The liquid was heated under reflux for 2 hours, and the solvent was then distilled off under reduced pressure. The residue was purified by a silica gel column chromatograph to obtain 2.9 g of 4-(3-chloro-2-hydroxypropyl)-1-diphenylmethylpiperazine and 2.8 g of 4-(2,3-epoxypropyl)-1-diphenylmethylpiperazine.

4-(3-Chloro-2-hydroxypropyl)-1-diphenylmethylpiperazine:

NMR δppm (CDCl$_3$): 2.2–2.9 (m,10H), 3.5–4.0 (m,3H), 4.20 (s,1H), 7.0–7.5 (m,10H)

4-(2,3-Epoxypropyl)-1-diphenylmethylpiperazine:

NMR δppm (CDCl$_3$): 2.1–2.8 (m,12H), 2.9–3.1 (m,1H), 4.20 (s,1H), 7.0–7.5 (m,10H)

(c) In 10 ml of dried THF were dissolved 170 mg of 5-hydroxy-6-methylquinoline synthesized in the preceding step (a) and 395 mg of 4-(3-chloro-2-hydroxypropyl)-1-diphenylmenhylpiperazine synthesized in the preceding step (b), and 143 mg of t-BuOK was then added thereto.

Afterward, the liquid was heated under reflux for 10 hours and was then poured into an aqueous ammonium chloride solution, and it was then extracted with chloroform. The extract was dried with anhydrous magnesium sulfate and then concentrated.

The residue was purified through a silica gel column 10 chromatcgraph by the use of an effluent solvent of chloroform:methanol=50:1, thereby obtaining 100 mg of 5-[3-(4-diphenylmethylpiperazine-1-yl)-2-hydroxypropoxy]-6-methylquinoline.

NMR δppm (CDCl$_3$): 3.46 (s,3H), 2.2–3.0 (m,10H), 3.7 (br,s,1H), 3.8–4.1 (m,2H), 4.0–4.2 (m,1H), 4.23 (s,1H), 7.7–7.0 (m,12H), 7.88 (d,1H), 8.60 (dd,1H), 8.86 (dd,1H)

EXAMPLE 24

5-[3-(4-Diphenylmethylpiperazine-1-yl)-2-hydroxypropoxy]-8-methylquinoline (a) Following the same procedure as in Example 23-(a), reaction and treatment were carried out using 3.9 g of 3-amino-4-methylphenol, 7 ml of glycerol, 8.7 g of sodium m-nitrobezene sulfonate and 29 ml of a 80% aqueous sulfuric acid solution in order to obtain 290 mg of 5-hydroxy-8-methylquinoline.

NMR δppm (DMSO-d$_6$): 6.8 (d,1H), 7.3 (d,1H), 7.3 (dd,1H), 8.5 (dd,1H), 7.8 (dd,1H), 10.0 (br,s,1H)

(b) Following the same procedure as in Example 23-(c), reaction and treatment were carried out using 360 mg of the above synthesized 5-hydroxy-8-methylquinoline, 1.39 g of 4-(3-chloro-2-hydroxypropyl)-1-diphenylmethylpiperazine and 300 mg of t-BuOK in order to obtain 120 mg of 5-[3-(4-diphenylmethylpiperazine-1-yl)-2-hydroxypropoxy]-8-methylquinoline.

IR νcm$^{-1}$ (KBr): 3350, 2900, 1610, 1580, 1540, 1430, 1360, 1270, 1230, 1200, 1080, 900, 800, 740, 690

NMR δppm (CDCl$_3$): 2.4–2.7 (m,10H), 3.79 (br,s,1H), 4.0–4.2 (m,3H), 4.2 (s,1H), 6.7 (d,1H), 7.1–7.4 (m,12H), 8.5 (dd,1H), 8.9 (dd.1H)

EXAMPLE 25

5-[3-(4-Diphenylmethylpiperazine-1-yl)-2-hydroxypropoxy]-8-methoxyquinoline (a) Following the same procedure as in Example 23-(a), reaction and treatment were carried out using 2.25 g of 3-amino-4-methoxyphenol, 3.7 ml of glycerol and sodium m-nitrobenzene sulfonate to obtain 180 mg of 5-hydroxy-8-methoxyquinoline.

NMR δppm (CDCl$_3$ +DMSO-d$_6$): 4.0 (s,3H), 6.90 (s,2H), 7.41 (dd,1H), 8.58 (dd,1H), 8.90 (dd,1H), 9.30 (br,1H)

(b) Following the same procedure as in Example 23-(c), reaction and treatment were carried out using 180 mg of 5-hydroxy-8-methoxyquinoline to obtain 140 mg of 5-[3-(4-diphenylmethylpiperazine-1-yl)-2-hydroxy-propoxy]-8-methoxyquinoline.

IR νcm$^{-1}$(KBr): 3360, 2500, 1620, 1580, 1540, 1470, 1440, 1400, 1370, 1280, 1100, 900, 800, 730

NMR δppm (CDCl$_3$): 2.5–2.8 (m,10H), 3.28 (br,s,1H), 4.03 (s,3H), 4.0–4.2 (m,2H), 4.24 (s,1H), 6.77 (d,1H), 6.90 (d,1H), 7.15–7.45 (m,11H), 8.54 (dd,1H), 8.93 (dd,1H)

EXAMPLE 26

5-[3-(4-Diphenylmethylpiperazine-1-yl)-2-hydroxypropoxy]-8-nitroquinoline

Following the same procedure as in Example 23-(c), reaction and treatment were carried out using 180 mg of 5-hydroxy-8-nitroquinoline to obtain 15 mg of the desired compound.

IR νcm$^{-1}$(KBr): 3350, 2900, 2400, 1610, 1570, 1510, 1420, 1310, 1270, 1180, 1080, 1000, 900, 730

NMR δppm (CDCl$_3$): 2.5–2.9 (m,10H), 4.2–4.3 (m,4H), 6.7 (d,1H), 7.1–7.4 (m,11H), 8.2 (d,1H), 8.7 (dd,1H), 9.1 (dd,1H)

EXAMPLE 27

5-[3-(4-Diphenylmethylpiperazine-1-yl)-2-hydroxypropylamino]quinoline

In 20 ml of chloroform were dissolved 1.11 g of 5-aminoquinoline and 1.19 g of 4-(3-chloro-2-hydroxypropyl)-1-diphenylmethylpiperazine, and the liquid was then heated at a temperature of 180° to 200° C. for 4 hours in an autoclave.

The reaction liquid was then concentrated, and the residue was purified through a silica gel column chromatograph by the use of ethyl acetate as an effluent solvent, thereby obtaining 460 mg of 5-[3-(4-diphenylmethylpiperazine-1-yl)-2-hydroxy-propylamino]quinoline.

IR νcm$^{-1}$(KBr): 3220, 2500, 1620, 1570, 1510, 1410, 1330, 1290, 1010

NMR δppm (CDCl$_3$): 2.2–2.8 (m,10H), 3.1–3.5 (m,2H), 3.6 (br,1H), 4.0–4.2 (m,1H), 4.21 (s,1H), 5.1 (br,1H), 6.57 (d,1H), 7.1–7.5 (m,12H), 8.25 (d,1H), 8.84 (d,1H)

EXAMPLE 28

5-[3-(4-Diphenylmethylpiperazine-1-yl)-2-hydroxypropylamino]-8-methoxyquinoline

Following the same procedure as in Example 27, reaction and treatment were carried out using 1.81 g of 5-amino-8 methoxyquinoline and 1.23 g of 4-(3-chloro-2-hydroxypropyl)-1-diphenylmethylpiperazine to obtain 200 mg of 5-[3-(4-diphenylmethylpiperazine- 1-yl)-2-hydroxy-propylamino]-8 methoxyquinoline.

IR νcm$^{-1}$(KBr): 3350, 2900, 2780, 1600, 1580, 1470, 1440, 1390, 1270, 1090, 990, 730, 690

NMR δppm (CDCl$_3$): 2.4–2.7 (m,10H), 3.09 (dd,1H), 3.30 (dd,1H), 4.0 (s,3H), 40–4.2 (m,1H), 4.22 (s,1H), 4.5 (br,1H), 6.54 (d,1H), 6.92 (d,1H), 7.1–7.4 (m,11H), 8.25 (dd,1H), 8.90 (dd,1H)

EXAMPLE 29

5-[3-(4-Diphenylmethylpiperazine-1-yl)-2-hydroxy-propoxy]-8-chloroquinoline

Following the same procedure as in Example 23-(c), reaction and treatment were carried out using 0.64 g of 8-chloro-5-hydroxyquinoline and 1.48 g of 4-chloro-2-hydroxypropyl)-1-diphenylmethylpiperazine synthesized in Example 23-(b), in order to obtain 0.68 g of 5-[3-(4-diphenylmethylpiperazine-1-yl)-2-hydroxy-propoxy]-8-chloroquinoline.

IR $\nu cm^{-1}$ (KBr): 3400, 2920, 2800, 1600, 1580, 1300, 1250, 1150, 1080, 1000

NMR $\delta$ppm (CDCl$_3$): 2.1–3.3 (m,10H), 4.0–4.2 (m,4H), 4.22 (s,1H), 6.70 (d,1H), 7.07–7.45 (m,11H), 7.67 (d,1H), 8.58 (dd,1H), 9.02 (dd,1H)

EXAMPLE 30

N-[3-(4-Diphenylmethylpiperazine-1-yl)-2-hydroxy-propyl]-N-methyl-5-quinolineamine (a) With 7.2 g of 5-aminoquinoline was mixed 40 ml of ethyl orthoformate, and the liquid was then heated under reflux for 5 hours. An excessive amount of ethyl orthoformate was distilled off, and the residue was then dissolved in 250 ml of anhydrous.ethanol. Afterward, 3.8 g of sodium boron hydride was added thereto under cooling with ice. The liquid was allowed to stand at room temperature overnight, and it was then heated at a temperature of 40° to 50° C. for 2 hours.

Afterward, the solvent was distilled off under reduced pressure, and water was then added to the liquid. The latter was extracted with methylene chloride, and the extract was then dried with anhydrous Glauber's salt. The solvent was distilled off, and the residue was then washed with ether to obtain 3.3 g of 5-(methylamino)quinoline.

NMR $\delta$ppm (CDCl$_3$): 3.05 (d,3H), 4.4 (dr,1H), 6.6 (dd,1H), 7.1–7.7 (m,3H), 8.2 (dd,1H), 8.8 (dd,1H)

(b) In 15 ml of THF was dissolved 0.59 g of the above synthesized 5-(methylamino)quinoline, and 2.36 ml of a 1.6M n-BuLi hexane solution was added thereto under cooling with ice. Next, a solution was added thereto which had been prepared by dissolving 1.42 g of 4-(3-chloro-2-hydroxypropyl)-1-diphenylmethylpiperazine in 8 ml of THF. Furthermore, 2.36 ml of a 1.6M n-BuLi hexane solution was added thereto, and the liquid was then allowed to stand at room temperature overnight. The reaction liquid was added to an aqueous ammonium chloride solution and was then extracted with methylene chloride.

The extract was dried with anhydrous magnesium sulfate and was then concentrated, and the residue was purified through a silica gel column chromatograph by the use of an effluent solvent of methylene chloride:methanol=20:1, thereby obtaining 230 mg of N-[3-(4-diphenylmethylpiperazine-1-yl)-2-hydroxypropyl]-N-methyl-5-quinolineamine.

IR $\nu cm^{-1}$ (KBr): 3400, 2600, 1630, 1590, 1450, 1410

NMR $\delta$ppm (CDCl$_3$): 2.1–2.6 (m,6H), 2.90 (s,3H), 3.00 (dd,1H), 3.19 (dd,1H), 3.59 (br,s,1H), 3.95–4.03 (m,1H), 4.20 (s,1H), 7.0–7.5 (m,12H), 7.58 (dd,1H), 7.85 (d,1H), 8.69 (d,1H), 8.86 (d,1H)

EXAMPLE 31

5-[3-(4-Diphenylmethylpiperazine-1-yl)-2-hydroxy-propylthio]quinoline

Following the same procedure as in Example 23-(c), reaction and treatment were carried out using 220 mg of 5-quinolinethiol and 1.2 g of 4-(3-chloro-2-hydroxypropyl)-1-(diphenylmethyl)piperazine, in order to obtain 130 mg of 5-[3-(4-diphenylmethylpiperazine-1-yl)-2-hydroxyProPylthio]quinoline.

NMR $\delta$ppm (CDCl$_3$): 2.2–2.7 (m,10H), 3.0–3.1 (m,2H), 3.9 (m,1H), 4.20 (s,1H), 7.1–7.8 (m,13H), 8.00 (d,1H), 8.75 (d,1H), 8.93 (d,1H)

EXAMPLE 32

5-[3-(4-Diphenylmethylpiperazine-1-yl)propoxy]quinoline (a) Following the same procedure as in Example 1-(a), reaction and treatment were carried out using 1.0 g of -hyroxyquinoline, 2.1 g of 1,3-dibromopropane and 0.78 g of t-BuOK as a base, in order to obtain 0.65 g of 5-(3-bromopropoxy)quinoline.

(b) Following the same procedure as in Example 1-(b), reaction and treatment were carried out using 0.65 g of the above synthesized bromo-compound and 0.62 g of N-diphenylmethylpiperazine, in order to obtain 0.65 g of 5-[3-(4-diphenylmethylpiperazine-1-yl)propoxy]quinoline.

IR $\nu cm^{-1}$(KBr): 3400, 1600, 1450, 1420, 1380, 1280, 1100

NMR $\delta$ppm (CDCl$_3$): 2.0–2.15 (t,2H), 2.3–2.7 (m,10H), 4.15 (t,2H), 4.23 (s,1H), 6.81 (d,1H), 7.16–7.7 (m,13H), 8.55 (d,1H), 8.88 (d,1H)

EXAMPLE 33

5-[4-(4-Diphenylmethylpiperazine-1-yl)butoxy]quinoline

Following the same procedure as in Example 32-(a), reaction and treatment were carried out using 1.0 g of 5-hydroxyquinoline and 2.3 g of 1,4-dibromobutane to obtain 0.78 g of 5-(4-bromobutoxy)quinoline. Furthermore, the same procedure as in Example 32-(b) was repeated with the exception that 0.78 g of N-diphenylmethylpiperazine was used, in order to perform reaction and treatment, so that 0.8 g of the desired compound was obtained.

IR $\nu cm^{-1}$(KBr): 3420, 1635, 1595, 1415, 1280

NMR $\delta$ppm (CDCl$_3$): 1.7–2.1 (m,4H), 2.3–2.8 (m,10H), 4.1–4.3 (m,3H), 6.8 (d,1H), 7.1–7.8 (m, 13H), 8.55 (d,1H), 8.9 (d,1H)

EXAMPLE 34

5-[2-(4-Diphenylmethylpiperazine-1-yl)ethoxy]quinoline

Following the same procedure as in Example 32-(a), reaction and treatment were carried out using 1.05 g of 5-hydroxyquinoline and 2.04 g of 1,2-dibromoethane to obtain 0.2 g of 5-(2-bromoethoxy)quinoline.

Furthermore, the same procedure as in Example 32-(b) was repeated with the exception that 0.2 g of N-diphenylmethylpiperazine was used, to perform reaction and treatment, so that 0.1 g of the desired compound was obtained.

NMR $\delta$ppm (CDCl$_3$): 2.4–3.2 (m,10H), 4.2–4.5 (m,3H), 6.85 (d,1H), 7.1–7.8 (m,13H), 8.5 (d,1H), 8.9 (d,1H)

EXAMPLE 35

5-[3-(4-Diphenylmethypiperazine-1-yl)propionamido]-quinoline (a) In 60 ml of methylene chloride was dissolved 4.5 g of 5-aminoquinoline, and 10.5 g of 3-chloropropionyl chloride and 9 g of triethylamine were then added thereto. After the liquid was allowed to stand at room temperature overnight, a 1N aqueous sodium hydroxide solution was added to the liquid, and the latter was then extracted with methylene chloride. The extract was washed twice with an aqueous sodium bicarbonate solution, was then dried, and was concentrated to obtain crystals. The latter were washed with methylene chloride, and filtered to obtain 2.2 g of 5-(3-chloropropionamido)quinoline in a crystalline state.

NMR δppm (CDCl$_3$): 2.9 (t,2H), 3.3 (s,1H), 3.9 (t,2H), 7.0–8.5 (m,5H), 8.9 (dd,1H)

(b) Following the same procedure as in Example 1-(b), 1.1 g of the above synthesized chloro-compound and 1.2 g of N-diphenylmethylpiperazine synthesized in Example 1-(b) were reacted and treated in an ethanol solvent to obtain 1.0 g of 5-[3-(4-diphenylmethylpiperazine-1-yl)propionamide)]quinoline.

IR νcm$^{-1}$(KBr): 3420, 2580, 1690, 1630, 1600, 1550, 1420, 1370, 1280

NMR δppm (CDCl$_3$): 2.4–3.9 (m,12H), 4.29 (s,1H), 7.1–7.5 (m,11H), 7.69 (t,1H), 7.88 (d,1H), 8.21 (d,1H), 8.35 (d,1H), 8.92 (d,1H), 11.09 (s,1H)

EXAMPLE 36

5-[3-(4-Dibenzosuberane-5-yl)piperazine-1-yl)propionamido]quinoline

Following the same procedure as in Example 1-(b), 1.1 g of the chloro-compound synthesized in Example 35-(a) and 1.32 g of N-(dibenzosuberane-5-yl)piperazine synthesized in Example 2-(a) were reacted and treated in an ethanol solvent to obtain 1.6 g of 5-[3-(4-dibenzosuberanylpiperazine-1-yl)propion-amido]quinoline.

IR νcm$^{-1}$(KBr): 3400, 2620, 1690, 1630, 1590, 1530, 1410, 1280

NMR δppm (CDCl$_3$): 2.2–3.0 (m,14H), 3.9–4.1 (m,3H), 7.0–7.2 (m,8H), 7.50 (dd,1H), 7.73 (t,1H), 7.92 (d,1H), 8.20 (d,1H), 8.46 (d,1H), 9.01 (d,1H), 11.1 (s,1H)

EXAMPLE 37

5-[N-Methyl-(3-(4-diphenylmethylpiperazine-1-yl)propionamido)]quinoline

In 30 ml of methylene chloride was dissolved 474 mg of 5-(methylamino)quinoline synthesized in Example 30-(a), and 850 mg of 3-chloropropionyl chloride and 0.5 ml of triethylamine were added thereto at room temperature. After standing at room temperature overnight, a 1N aqueous sodium hydroxide solution was then added to the liquid so as to alkalinize it. The alkaline liquid was extracted with methylene chloride, and the extract was then washed twice with an aqueous sodium bicarbonate solution and dried with anhydrous magnesium sulfate. The solvent was distilled off under reduced pressure, and 756 mg of N-(diphenylmethyl)-piperazine was added to the residue. The liquid was reacted and treated in an ethanol solvent in accordance with the same procedure as in Example 1-(b) to obtain 880 mg of 5-[N-methyl-(3-(4-diphenylmethylpiperazine-1-yl)propionamido)]quinoline.

IR νcm$^{-1}$(KBr): 3400, 2520, 1650, 1500, 1410, 1120
NMR δppm (CDCl$_3$): 1.9–2.50 (m,10H), 2.64 (br,t,2H),
3.34 (s,3H), 4.13 (s,1H), 7.0–7.5 (m,12H), 7.72 (dd,1H), 8.1–8.2 (m,2H), 8.97 (dd,1H)

EXAMPLE 38

5-[N-Methyl-(3-(4-dibenzosuberane-5-yl)propionamide)]quinoline

Following the same procedure as in Example 37, 474 mg of 5-(methylamino)quinoline was reacted with 850 mg of 3-chloropropionyl chloride. The reaction product was reacted and treated with 834 mg of N-(dibenzosuberane-5 yl)piperazine synthesized in Example 2-(a) in an ethanol solvent in accordance with the same procedure as in Example 2-(a), in order to obtain 1.02 g of 5-[N-methyl-(3-(4-dibenzosuberanylpiperazine-1-yl)-propionamide)]quinoline.

IR νcm$^{-1}$(KBr): 3400, 2900, 2500, 1650, 1590, 1410, 1120

NMR δppm (CDCl$_3$): 1.7 (br,1H), 1.8–2.4 (m,12H), 2.5–2.6 (m,2H), 2.6–2.9 (m,2H), 3.34 (s,3H), 3.86 (s,1H), 3.8–4.0 (m,2H), 7.0–7.7 (m,13H), 8.1–8.15 (m,2H), 8.98 (dd,1H)

EXAMPLE 39

5-[N-Acetyl-(2-acetoxy-3-(4-diphenylmethylpiperazine-1-yl)propylamino)]quinoline In 4.5 g of acetic anhydride was dissolved 1.0 g of 5-[3-(4-diphenylmethylpiperazine-1-yl)-2-hydroxypropylamino]quinoline synthesized in Example 27, and the liquid was then allowed to stand overnight. Afterward, the liquid was poured into an aqueous sodium bicarbonate solution, and it was then extracted with methylene chloride. The extract was dried with anhydrous magnesium sulfate and then concentrated, and the residue was purified through a silica gel column chromatograph by the use of ethyl acetate as an effluent solvent to obtain 1.05 g of the desired compound.

NMR δppm (CDCl$_3$): 1.69 (s,3H), 1.77 (s,3H), 2.1–2.7 (m,8H), 3.37 (dd,1H), 3.69 (dd,1H), 4.10 (s,1H), 3.34 (dd,1H), 3.61 (dd,1H), 4.61 (dd,1H)

EXAMPLE 40

5-[N-Acetyl-(3-(4-diphenylmethylpiperazine-1-yl)-2-hydroxypropylamino)]quinoline In a mixed solvent of 10 ml of methanol and 5 ml of water were dissolved 0.55 g of 5-[N-acetyl-(2-acetoxy-3-(4-diphenylmethylpiperazine-1-yl)propylamino)]-quinoline and 0.5 g of potassium carbonate, and the liquid was allowed to stand at room temperature overnight. The liquid was extracted with methylene chloride, and the extract was then dried with anhydrous magnesium sulfate and was concentrated to obtain 0.5 g of the desired compound.

NMR δppm (CDCl$_3$): 1.74 (s,1H), 2.1–2.9 (m,10H), 3.4–3.6 (m,1H), 3.8–4.2 (m,3H), 7.1–7.8 (m,13H), 8.1–8.3 (m,2H), 8.96–8.99 (m,1H)

EXAMPLE 41

2-Chloro-5-[3-(4-diphenylmethylpiperazine-1-yl)-2-hydroxypropoxy]quinoline

Following the same procedure as in Example 23-(c), reaction and treatment were carried out using 1 g of 2-chloro-5-hydroxyquinoline and 2.88 g of 4-(3-chloro-2-hydroxypropyl)-1-diphenylmethylpiperazine synthesized in Example 23-(b), in order to obtain 1.39 g of 2-chloro-5-[3-(4-diphenylmethylpiperazine-1-yl)-2-hydroxypropoxy]quinoline.

NMR δppm (DMSO-d6): 2.2–2.4 (m,4H), 2.4–2.7 (m,6H), 3.9–4.3 (m,4H), 4.91 (s,1H), 6.9–7.7 (m,14H), 8.64 (d,1H)

EXAMPLE 42

5-[3-(4-Diphenylmethylpiperazine-1-yl)-2-hydroxypropoxy]-2-methoxyquinoline

Following the same procedure as in Example 23-(c), reaction and treatment were carried out using 0.6 g of 5-hydroxy-2-methoxyquinoline and 1.93 g of 4-(3-chloro-2-hydroxypropyl)-1-diphenylmethylpiperazine synthesized in Example 23-(b), in order to obtain 1.2 g of 5-[3-(4-diphenylmethylpiperazine-1-yl)-2-hydroxypropoxy]-2-methoxyquinoline.

NMR δppm (DMSO-d6): 2.2–2.7 (m,4H), 2.4–2.7 (m,6H), 3.9–4.15 (m,6H), 4.19 (s,1H), 4.83 (s,1H), 6.75–6.9 (m,2H), 7.05–7.55 (m,12H), 8.46 (d,1H)

EXAMPLE 43

5-[3-(4-Diphenylmethylpiperazine-1-yl)-2-hydroxypropoxy]isoquinoline (a) With 40 ml of acetone were mixed 3.55 g of 5-hydroxyisoquinoline, 3.4 g of epichlorohydrin and 5.0 g of potassium carbonate, and the liquid was then heated under reflux for 6 hours. After the removal of insoluble substances, the solvent was distilled off, and the resultant residue was purified through a silica gel column chromatograph. On allowing an effluent solvent of chloroform:methanol=100:1 to flow therethrough, 5-(2,3-epoxypropoxy)isoquinoline which was the desired product was obtained in an oily state in an amount of 1.6 g.

IR νcm$^{-1}$(liq. film): 3480, 2920, 1670, 1580, 1490, 1390, 1280, 1250

(b) In 20 ml of ethanol were dissolved 0.8 g of the above obtained epoxy compound and 1.0 g of N-diphenylmethylpiperazine, and the liquid was then heated under reflux for 2 hours. After the reaction, the solvent was distilled off, and the resultant residue was purified through a silica gel column chromatograph. On allowing an effluent solvent of chloroform:methanol=50:1 to flow therethrough, 5-[3-(4-diphenylmethylpiperazine-1-yl)-2-hydroxypropoxy]isoquinoline which was the intended product was obtained in an powdery state in an amount of 0.7 g.

IR νcm$^{-1}$(KBr): 3420, 2820, 1620, 1580, 1490, 1450

NMR δppm (CDCl3): 2.2–3.0 (m,10H), 3.8 (s,1H), 4.15 (s,2H), 4.25 (s,2H), 6.9–7.8 (m,13H), 8.0 (d,1H), 8.5 (d,1H), 9.2 (d,1H)

EXAMPLE 44

5-[3-(4-(Dibenzosuberane-5-yl)piperazine-1-yl)-2-hydroxypropoxy]isoquinoline

In 20 ml of ethanol were dissolved 0.93 g of the epoxy compound prepared in Example 43-(a) and 1.29 g of the piperazine compound prepared in Example 2-(a), and the liquid was then heated under reflux for 2 hours. After the reaction, the solvent was distilled off, and the resultant residue was purified through a silica gel column chromatograph. On allowing an effluent solvent of chloroform:methanol=50:1 to flow therethrough, the desired product 5-[3-(4-(dibenzosuberane-5-yl)piperazine-1-yl)-2-hydroxypropoxy]isoquinoline was obtained in an powdery state in an amount of 1.14 g.

IR νcm$^{-1}$(KBr): 3400, 2920, 2800, 1580, 1490, 1430, 1390, 1280, 1110

NMR δppm (CDCl3): 2.1–3.0 (m,12H), 3.6–4.4 (m,7H), 6.9–7.6 (m,11H), 8.0 (d,1H), 8.5 (m,1H), 9.15 (s,1H)

EXAMPLE 45

5-[3-(4-Diphenylmethylhomopiperazine-1-yl)-2-hydroxypropoxy]isoquinoline

In 20 ml of ethanol were dissolved 0.74 g of the epoxy compound prepared in Example 43-(a) and 0.97 g of N-diphenylmethylhomopiperazine, and the liquid was then heated under reflux for 2 hours. After the reaction, the solvent was distilled off, and the resultant residue was purified through a silica gel column chromatograph. On allowing an effluent solvent of chloroform:methanol=50:1 to flow therethrough, the desired product 5-[3-(4-diphenylmethylhomopiperazine-1-yl)-2-hydroxypropoxy]isoquinoline was obtained in an powdery state in an amount of 1.04 g.

NMR δppm (CDCl3): 1.8 (t,2H), 2.3–3.3 (m,10H), 4.0 (s,1H), 4.15 (s,3H), 4.55 (s,1H), 6.8–7.7 (m,13H), 8.0 (d,1H), 8.5 (dd,1H), 9.15 (s,1H)

EXAMPLE 46

4-[3-(4-Diphenylmethylpiperazine-1-yl)-2-hydroxypropoxy]quinoline

In 50 ml of acetone were dissolved 3.55 g of 4-hydroxyquinoline, 3.4 g of epichlorohydrin and 5 g of potassium carbonate, and the liquid was then heated under reflux for 6 hours. After the removal of insoluble substances, the solvent was distilled off, and the resultant residue was then purified through a silica gel column chromatograph.

On allowing an effluent solvent of chloroform:methanol=100:1 to flow therethrough, 2.1 g of 4-(2,3-epoxypropoxy)quinoline was obtained in an oily state. In 40 ml of ethanol were dissolved 1.6 g of this epoxy compound and 2.0 g of N-diphenylmethylpiperazine, and the liquid was then heated under reflux for 2 hours. After the reaction, the solvent was distilled off, and the resultant residue was purified in a silica gel column chromatograph. On allowing an effluent solvent of chloroform:methanol=50:1 to flow therethrough, the desired product 4-[3-(4-diphenylmethylpiperazine-1-yl)-2-hydroxypropoxy]quinoline was obtained in a powdery state in an amount of 1.5 g.

IR νcm$^{-1}$(KBr): 3400, 2800, 1630, 1580, 1490, 1450, 1230, 1010

NMR δppm (CDCl3): 2.0–3.0 (m,10H), 3.5–3.9 (m,1H), 3.9–4.6 (m,3H), 5.85 (d,1H), 6.9–7.8 (m,14H), 8.1 (d,1H)

EXAMPLE 47

8-[3-(4-Diphenylmethylpiperazine-1-yl)-2-hydroxypropoxy]isoquinoline

In 15 ml of dried THF were dissolved 80 mg of 8-hydroxyisoquinoline and 204 mg of 4-(3-(chloro-2-hydroxypropyl)-1-diphenylmethylpiperazine synthesized in Example 23-(b), and 68 mg of potassium t-butoxide was further added thereto, followed by stirring at room temperature for 20 hours. The reaction liquid was then poured into 15 ml of an aqueous saturated ammonium chloride solution, and extraction was then performed with 150 ml of methylene chloride. After drying with an anhydrous Glauber's salt, the solvent was distilled off, and the resultant residue was purified through a silica gel thin-layer chromatograph. Development was carried out by the use of an effluent solvent of chloroform:methanol=25:1 for the purpose of separation and purification, with the result that 8-[3-(4-diphenylmethylpiperazine-1-yl)-2-hydroxy-propoxy]isoquinoline was obtained in an amount of 70 mg.

IR $\nu cm^{-1}$(KBr): 3400, 2800, 1570, 1450, 1390, 1280, 1120

NMR $\delta$ppm (CDCl$_3$): 2.4–3.0 (m,10H), 3.7 (br,s,1H), 4.0–4.5 (m,4H), 6.96 (d,1H), 7.1–7.8 (m,13H), 8.56 (d,1H), 9.60 (s,1H)

EXAMPLE 48

1-[3-(4-Diphenylmethylpiperazine-1-yl)-2-hydroxypropoxy]isoquinoline

In 20 ml of of dried DMF was dissolved 1 g of 1-hydroxyisoquinoline, and 0.77 g of t-butoxypotassium was further added thereto. The liquid was then heated with stirring at 50° C. for 30 minutes. To the reaction liquid was added 1.91 g of epichlorohydrin, and heating was further made with stirring at 90° C. for 2 hours. The solvent was distilled off under reduced pressure, and ethanol was added to the resultant residue. Afterward, a deposited salt was removed by filtration, and active carbon was then added to the ethanol solution so as to purify the latter. The amount of the ethanol solution was then adjusted to 30 ml and 1 g of diphenylmethylpiperazine was added thereto, and the liquid was then heated under reflux for 2.5 hours. The solvent was distilled off, and the resultant residue was then purified by mesns of a silica gel column chromatograph. On allowing an effluent solvent of chloroform:methanol=50:1 to flow therethrough, the intended product 1-[3-(4-diphenylmethylpiperazine-1-yl)-2-hydroxypropoxy]isoquinoline was obtained in a powdery state in an amount of 1.94 g.

NMR $\delta$ppm (CDCl$_3$): 2.0–2.8 (m,8H), 2.9 (d,2H), 3.4–4.5 (m,5H), 6.5 (dd,1H), 6.8–7.9 (m,14H), 8.4 (dd,1H)

EXAMPLE 49

8-[3-(4-Diphenylmethylpiperazine-1-yl)-2-hydroxypropoxy]-quinoline

In 5 ml of dried THF were dissolved 200 mg of 8-hydroxyquinoline and 319 mg of the piperazine compound prepared in Example 23-(b), and 120 mg of potassium t-butoxide was further added thereto. The liquid was then stirred at room temperature for 5 days, and 20 ml of a 1N aqueous sodium hydroxide solution was poured into the liquid, followed by extracting with 100 ml of methylene chloride. Afterward, the methylene chloride solution was washed with a dilute aqueous sodium hydroxide solution, and was then dried with an anhydrous Glauber's salt. After the solvent was distilled off, the residue was purified through a silica gel column chromatograph. On allowing an effluent solvent of chloroform:methanol=50:1 to flow therethrough, the desired product 8-[3-(4-diphenylmethylpiperazine-1-yl)-2-hydroxypropoxy]-quinoline was obtained in a powdery state in an amount of 45 mg.

IR $\nu cm^{-1}$(KBr): 3350, 2800, 1500, 1450, 1320, 1110

NMR $\delta$ppm (CDCl$_3$): 2.2–3.0 (m,10H), 4.1–4.8 (m,4H), 4.9 (br,s,1H), 7.0–7.8 (m,14H), 8.15 (dd,1H), 8.85 (d,d,1H)

EXAMPLE 50

5-[3-(4-Diphenylmethylpiperazine-1-yl)-2-hydroxypropoxy]quinoxaline

In 20 ml of dried DMF was dissolved 1 g of 5-hydroxyquinoxaline, and 0.78 g of t-butoxypotassium was further added. Afterward, the liquid was heated with stirring at 50° C. for 30 minutes. After the reaction, 1.9 g of epichlorohydrin was added thereto, followed by heating and stirring at 90° C. for 3 hours. The solvent was distilled off under reduced pressure and water was then added to the resultant residue, and the liquid extracted with 50 ml of chloroform. The chloroform liquid was dried with an anhydrous Glauber's salt, followed by distilling off, and the residue was then purified through a silica gel column chromatograph. On allowing an effluent solvent of chloroform:methanol=100:1 to flow therethrough, 0.28 g of 5-(2,3-expoypropoxy)-quinoxaline was obtained in an oily state. In 10 ml of ethanol were dissolved 0.28 g of this epoxy compound and 0.35 g of N-diphenylmethylpiperazine, and the liquid was then heated under reflux for 3 hours. After the reaction, the solvent was distilled off, and the resultant residue was then purified by means of a silica gel column chromatograph. On allowing a solvent of chloroform:methanol=50:1 to flow therethrough, the desired compound 5-[3-(4-diphenylmethylpiperazine-1-yl)-2-hydroxypropoxy]quinoxaline was obtained in a powdery state in an amount of 0.12 g.

IR $\nu cm^{-1}$(KBr): 3360, 2980, 1600, 1560, 1480, 1460, 1440, 1290, 1100

NMR $\delta$ppm (CDCl$_3$): 2.2–3.2 (m,10H), 3.8 (s,1H), 4.1–4.6 (m,4H), 7.0–8.0 (m,13H), 8.7–9.1 (m,2H)

EXAMPLE 51

5-[3-(4-Diphenylmethylpiperazine-1-yl)-2-hydroxypropoxy]quinazoline

In 30 ml of dried DMF was dissolved 2 g of 5-hydroxyqunazoline, and 1.5 g of t-butoxypotassium was added thereto, followed by heating and-stirring at 50° C. for 1 hour. To the reaction liquid was added 4 g of epichlorohydrin, and the liquid was then heated with stirring at 90° C. for 3 hours. The solvent was distilled off under reduced pressure, and the resultant residue was then purified by the use of a silica gel column chromatograph. On allowing an effluent solvent of chloroform:methanol=100:1 to flow therethrough, 5-(2,3-epxoypropoxy)quinazoline was obtained in an oily state in an amount of 0.84 g. In 20 ml of ethanol were dissolved 0.84 g of this epoxy compound and 1.05 g of N-diphenylmethylpiperazine, and the liquid was then heated under reflux for 3 hours. After the reaction, the solvent was distilled off, and the resultant residue was then purified through the silica gel column chromatograph. On allowing the effluent solvent of chloroform:methanol=50:1 to flow therethrough, the intended product 5-[3-(4-diphenylmethylpiperazine-1-yl)-2-hydroxypropoxy]quinazoline was obtained in a powdery state in an amount of 0.48 g.

IR $\nu cm^{-1}$(KBr): 3400, 2800, 1610, 1580, 1130

NMR $\delta$ppm (CDCl$_3$): 2.2–3.0 (m,10H), 3.4 (br,s,1H), 2.0–2.3 (m,4H), 6.9–7.9 (m,13H), 9.28 (s,1H), 9.70 (s,1H)

EXAMPLE 52

5-(3-[4-((4-Pyridyl)-phenylmethyl)piperazine-1-yl]-2-hydroxypropoxy)-quinoline

Following the same procedure as in Example 1-(b), reaction and treatment were carried out using N-[(4-pyridyl)-phenylmethyl]piperazine to obtain the desired compound.

IR $\nu$cm$^{-1}$(KBr): 3350, 1620, 1590, 1410, 1370, 1270, 1100, 780

NMR $\delta$ppm (CDCl$_3$): 2.3–3.9 (m,10H), 4.05–4.20 (m,3H), 4.25 (s,1H), 6.85 (d,1H), 7.2–7.4 (m,8H), 7.58 (t,1H), 7.70 (d,1H), 8.50 (d,1H), 8.55 (d,1H), 2.89 (d,1H)

EXAMPLE 53

2,4-Dimethyl-5-[3-((α,α-diphenylacetyl)piperazine-1-yl)-2-hydroxypropoxy]quinoline Following the same procedure as in Example 1-(a) and (b), reaction and treatment were carried out using 2,4-dimethyl-5-hydroxyquinoline prepared in Example 5-(b) and N-(α,α-diphenylacetyl)piperazine in order to obtain the desired compound.

IR $\nu$cm$^{-1}$(KBr) (HCl salt): 3350 (br.), 1630, 1595, 1430, 1380, 1260, 1090, 1025, 735, 690

NMR 270 MHz (CDCl$_3$) $\delta$ppm: 2.10–2.72 (m,5H), 2.63 (s,3H), 2.83 (s,3H), 3.30–3.60 (m,3H), 3.60–3.80 (m,2H), 4.00–4.20 (m,2H), 5.19 (s,1H), 6.75 (d,1H), 6.99 (s,1H), 7.20–7.40 (m,10H), 7.47 (tr,1H), 7.60 (d,1H)

EXAMPLE 54

2-Trifluoromethyl-4-methyl-5-[3-(4-(dibenzosuberane-5-yl)piperazine-1-yl)-2-hydroxypropoxy]quinoline The same procedures as in Example 5-(a) and (b) were repeated with the exception that acetylacetone was replaced with α,α,α-trifuloroacetylacetone, in order to perform reaction and treatment, whereby 2-trifluoromethyl-4-methyl-5-hydroxyquinoline was obtained.

Furthermore, following the same procesures as in Example 1-(a) and (b), reaction and treatment were carried out using the thus prepared compound and N-(dipenzosuberane-5-yl)piperazine to obtain the desired compound.

IR $\nu$cm$^{-1}$(KBr): 2920, 2800, 1590, 1370, 1350, 1330, 1270, 1180, 1140, 750

NMR (CDCl$_3$) $\delta$ppm: 2.20–2.90 (m,12H), 2.76 (s,3H), 3.90–4.25 (m,6H), 6.95–7.20 (m,9H), 7.55–7.75 (m,3H)

EXAMPLE 55

2-Trifluoromethyl-4-methyl-5-[3-(4-(α,α-diphenylacetyl)piperazine-1-yl)-2-hydroxypropoxy]-quinoline Following the same procedures as in Example 1-(a) and (b), reaction and treatment were carried out using 2-trifluoromethyl-4-methyl-5-hydroxyquinoline prepared in Example 54 and N-(α,α-diphenylacetyl)piperazine in order to obtain the desired compound.

IR $\nu$cm$^{-1}$(KBr): 1630, 1595, 1450, 1430, 1380, 1350, 1270, 1180, 1140

NMR (CDCl$_3$) $\delta$ppm: 215–270 (m,6H), 2.77 (s,3H), 3.40–3.55 (m,2H), 3.65–3.80 (m,2H), 4.00–4.30 (m,3H), 5.20 (s,1H), 7.00 (d,1H, J=7.41), 7.10–7.50 (m,10H), 7.60–7.80 (m,3H)

EXAMLE 56

2-Trifluoromethyl-4-methyl-5-[3-(4-diphenylmethyl-piperazine-1-yl)-2-hydroxypropoxy]quinoline Following the same procedures as in Example 1-(a) and (b), reaction and treatment were carried out using 2-trifluoromethyl-4-methyl-5-hydroxyquinoline prepared in Example 54 and N-diphenylmethylpiperazine in order to obtain the desired compound.

IR $\nu$cm$^{-1}$(KBr): 2800, 1595, 1450, 1380, 1350, 1330, 1270, 1180, 1140

NMR $\delta$(CDCl$_3$) ppm: 2.20–2.90 (m,10H), 2.77 (s,3H), 4.00–4.35 (m,4H), 7.02 (d,1H, J=7.92Hz), 7.10–7.55 (m,10H), 7.55–7.80 (m,3H)

EXAMPLE 57

5-(3-[4-(Bis(4-fluorophenyl)methyl)piperazine-1-yl]-2-hydroxypropoxy)quinoline

Following the same procedure as in Example 1-(b), reaction and treatment were carried out using the epoxy compound prepared in Example 1-(a) and N-[bis-(4-fluorophenyl)methyl]piperazine in order to obtain the desired compound.

IR (KBr) $\nu$max cm$^{-1}$(HCl salt): 3400, 1630, 1590, 1510, 1410, 1280, 1230

NMR $\delta$ppm (CDCl$_3$): 2.1–2.9 (10H, bm), 4.1–4.2 (3H,m), 6.85–7.75 (12H,m), 8.55 (1H,dd), 8.9 (1H,dd)

EXAMPLE 58

5-(3-[4-((4-Chlorophenyl)-phenylmethyl)piperazine-1-yl]-2-hydroxypropoxy)quinoline Following the same procedure as in Example 1-(b), reaction and treatment were carried out using the epoxy compound prepared in Example 1-(a) and N-[(4-chlorophenyl)phenylmethyl]piperazine in order to obtain the desired compound.

IR (KBr) $\nu$max cm$^{-1}$ (HCl salt): 3400, 1630, 1590, 1410, 1380, 1280

NMR (CDCl$_3$) $\delta$ppm: 2.17–2.93 (10H,bm), 4.1–4.3 (4H,m), 6.85 (1H,d), 7.16–7.74 (12H,m), 8.55 (1H,dd), 8.9 (1H,dd)

EXAMPLE 59

5-(3-[4-(Bis-(4-methoxyphenyl)methyl)piperazine-1-yl]-2-hydroxypropoxy)quinoline Following the same procedure as in Example 1-(b), reaction and treatment were carried out using the epoxy compound prepared in Example 1-(a) and N-[4-bis-(4-methoxyphenyl)methyl]piperazine in order to obtain the desired compound.

IR $\nu$max cm$^{-1}$(KBr): 3400, 1635, 1610, 1595, 1510, 1410, 1280, 1250

NMR (CDCl$_3$) $\delta$ppm: 2.34–2.76 (10H, bm), 3.75 (6H,s), 4.11–4.24 (4H,m), 6.80–6.87 (5H,m), 7.26–7.39 (5H,m), 7.55–7.71 (2H,m), 8.57 (1H,d), 8.89 (1H,dd)

EXAMPLE 60

5-[3-(4-(Iminodibenzyl-5-carbonyl)piperazine-1-yl)-2-hydroxypropoxy]quinoline

Following the same procedure as in Example 1-(b), reaction and treatment were carried out using the epoxy compound prepared in Example 1-(a) and N-(iminodibenzyl-5-carbonyl)piperazine in order to obtain the desired compound.

IR $\nu$max cm$^{-1}$(KBr) (HCl salt): 3400, 1640, 1600, 1490, 1415, 1380, 1280

NMR (CDCl₃) δppm: 2.3–2.4 (2H,m), 2.53–2.61 (4H,m), 3.15 (4H,s), 3.40 (4H,m), 4.10–4.22 (3H,m), 6.85 (1H,d), 7.09–7.71 (11H,m), 8.52 (1H,dd), 8.90 (1H,dd)

EXAMPLE 61

2,4-Dimethyl-5-[3-(4-(iminodibenzyl-5-carbonyl)piperazine-1-yl)-2-hydroxypropoxy]quinoline Following the same procedure as in Example 1-(b), reaction and treatment were carried out using the epxoy compound prepared in Example 5 and N-(iminodibenzyl-5-carbonyl)piperazine in order to obtain the desired compound.

IR νmax cm⁻¹(KBr) (HCl salt): 3400, 3240, 1640, 1600, 1480, 1440, 1390, 1270, 1260

NMR δppm (CDCl₃): 1.8–2.15 (1H,m), 2.26–2.40 (2H,m), 2.50–2.60 (4H,m), 2.64 (3H,s), 2.84 (3H,s), 3.16 (4H,s), 3.40 (4H,s), 4.01–4.20 (3H,m), 6.77 (1H,d), 6.99 (1H,s), 7.09–7.62 (10H,m)

EXAMPLE 62

5-[3-(N'-(Dibenzosuberane-5-yl)ethylenediamino)-2-hydroxypropoxy]quinoline

Following the same procedure as in Example 1-(b), reaction and treatment were carried out using the epxoy compound prepared in Example 1-(a) and N-(dibenzosuberane-5-yl)ethylenediamine in order to obtain the desired compound.

IR νmax cm⁻¹(KBr) (HCl): 3400, 2920, 1630, 1590, 1410, 1380, 1280, 1100

NMR δppm (CDCl₃): 2.20–2.59 (2H, bs), 2.60–3.0 (8H,m), 3.56–3.72 (2H,m), 4.04–4.25 (3H,m), 4.77 (1H,s), 8.82 (1H,d), 7.08–7.75 (11H,m), 8.53 (1H,dd), 8.87 (1H,dd)

EXAMPLE 63

5-[3-(N,N'-Dimethyl-N'-(dibenzosuberan-5-yl)ethylenediamino-2-hydroxypropoxy]quinoline Following the same procedure as in Example 1-(b), reaction and treatment were carried out using the epoxy compound prepared in Example 1-(a) and N,N'-dimethyl-N'-(dibenzosuberane-5-yl)ethylenediamine in order to obtain the desired compound.

IR νmax cm⁻¹(KBr) (HCl salt): 3400, 2920, 1630, 1590, 1470, 1410, 1370, 1280, 1100

NMR δppm (CDCl₃): 2.13 (6H,d), 2.4–2.55 (5H,m), 2.56–2.90 (3H,m), 3.90–4.20 (6H,m), 6.85 (1H,d), 6.98–7.75 (11H,m), 8.57 (1H,dd), 8.92 (1H,dd)

EXAMPLE 64

2-Methylthio-5-[3-(4-(dibenzosuberane-5-yl)piperazine-1-yl)-2-hydroxypropoxy]quinoline An epoxy compound was prepared from 2-methylthio-5-hydroxyquinoline in accordance with the same procedure as in Example 1-(a), and reaction and treatment were then carried out using this epoxy compound and N-(dibenzosuberane-5-yl)piperazine to obtain the desired compound.

IR νcm⁻¹(KBr) (HCl salt): 1615, 1600, 1575, 1480, 1440, 1390, 1335, 1285, 1250, 1125

NMR δppm (CDCl₃): 2.20–2.85 (m,12H), 2.67 (s,3H), 3.85–4.20 (m,6H), 6.74 (d,1H,J=8.9), 6.95–7.30 (m,9H), 7.40–7.55 (m,2H), 8.26 (d,1H,J=8.9)

EXAMPLE 65

2-Methylthio-5-[3-(4-(α,α-diphenylacetyl)piperazine-1-yl)-2-hydroxypnopoxy]quinoline An epoxy compound was prepared from 2-methylthio-5-hydroxyquinoline in accordance with the same procedure as in Example 1-(a), and reaction and treatment were then carried out using this epoxy compound and N-(α,α-diphenylacetyl)piperazine to obtain the desired compound.

IR (KBr) νcm⁻¹(HCl salt): 1630, 1580, 1440, 1420, 1390, 1250, 1130, 1070, 1020

NMR 270 MHz (CDCl₃) δppm: 2.15–2.25 (m,1H), 2.35–2.70 (m,5H), 2.68 (s,3H), 3.40–3.55 (m,2H), 3.65–3.80 (m,2H), 4.05–4.20 (m,3H), 6.75 (d,1H,J=8.4), 7.15–7.35 (m,11H), 7.45–7.55 (m,2H), 8.38 (d,1H,J=8.91)

EXAMPLE 66

2,4-Dimethyl-5-[3-(N,N'-dimethyl-N'-(dibenzosuberane-5-yl)ethylenediamino)-2-hydroxypropoxy]quinoline Following the same procedure as in Example 1-(b), reaction and treatment were carried out using the epxoy compound prepared in Example 5 and N,N'-dimethyl-N'-(dibenzosuberane-5-yl)ethylenediamine in order to obtain the desired compound.

NMR (CDCl₃) δppm: 2.12 (6H,d), 2.40–2.6 (5H,m), 2.65 (3H,s), 2.70–2.90 (8H,m), 3.93–4.10 (6H,m), 6.77 (1H,d), 7.00–7.20 (9H,m), 7.45–7.65 (2H,m)

EXAMPLE 67

2,4-Dimethyl-5-[3-(4-diphenylmethylenepiperizine-1-yl)-2-hydroxypropoxy]quinoline Following the same procedure as in Example 1-(b), reaction and treatment were carried out using the epoxy compound prepared in Example 5 and 4-diphenylmethylenepiperizine to obtain the desired compound.

IR (KBr) νmax cm⁻¹(HCl salt): 3380, 2900, 2640, 1630, 1600, 1470, 1440, 1380, 1270

NMR (CDCl₃) δppm: 1.74–1.97 (1H,bm), 2.35–2.60 (6H,m), 2.62–2.95 (10H,m), 4.05–4.30 (3H,m), 6.80 (1H,d), 7.00 (1H,s), 7.10–7.35 (10H,m), 7.45–7.65 (2H,m)

EXAMPLE 68

5-(3[N-{3-dibenzosuberane-5-ylidene)propy}-N-methylamino-2-hydroxypropoxy)quinoline Following the same procedure as In Example 1-(b), reaction and treatment were carried out using the epoxy compound prepared in Example 1-(a) and hydroxydibenzosuberane in order to obtain the desired compound.

IR (KBr) νmax cm⁻¹ (HCl salt): 3360, 2640, 1630, 1590, 1475, 1410, 1370, 1270, 1100

NMR (CDCl₃) δppm: 1.45–2.05 (5H, bm), 2.28 (3H,s), 2.31–2.85 (6H,m), 3.2–3.5 (1H,bm), 4.05–4.35 (3H,m), 6.8–7.76 (12H,m), 8.52–8.58 (1H,m), 8.89–8.93 (1H,m)

EXAMPLE 69

5-[3-(3,3-Diphenylpropylamino)-2-hydroxypropoxy]quinoline

Following the same procedure as in Example 1-(b), reaction and treatment were carried out using the epxoy compound prepared in Example 1-(a) and 3,3-diphenyl-propylamine to obtain the desired compound.

IR (KBr) νcm⁻¹: 1610, 1580, 1490, 1460, 1400, 1360, 1315, 1270, 1200, 1170, 1140

NMR 270 (CDCl₃) δppm: 2.43–2.60 (m,2H), 2.80–3.15 (m,3H), 4.90–5.20 (m,5H), 6.67 (d,1H,J=7.42), 7.05–7.40 (m,11H), 7.45–7.80 (m,2H), 8.53 (d,1H,J=8.4), 8.80–8.95 (m,1H)

EXAMPLE 70

5-[3-(2,2-Diphenylethylamino)-2-hydroxypropoxy]-quinoline

Following the same procedure as in Example 1-(b), reaction and treatment were carried out using the epoxy compound prepared in Example 1-(a) and 2,2-diphenylethylamine in order to obtain the desired compound.

IR (KBr) νcm⁻¹ (HCl salt): 1620, 1580, 1480, 1440, 1400, 1370, 1270, 1200, 1170, 1140

NMR 270 (CDCl₃) δppm: 2.85–3.40 (m,3H), 4.00–4.28 (m,5H), 6.82 (d,1H,J=7.42), 7.05–7.40 (m,1H), 7.52–7.72 (m,2H), 8.45–8.55 (m,1H), 8.85–8.90 (m,1H)

EXAMPLE 71

2-Methylsufonyl-5-[3-(4-(dibenzosuberane-5-yl)piperazin-1-yl)-2-hydroxypropoxy]quinoline An epoxy compound was prepared from 2-methylsulfonyl-5-hydroxyquinoline in accordance with the same procedure as in Example 1-(a), and reaction and treatment were then made using the thus prepared epoxy compound and N-(dibenzosuberane-5-yl)piperazine to obtain the desired compound.

IR (KBr) νcm⁻¹: 1640, 1610, 1575, 1465, 1450, 1300, 1270, 1160, 1140, 1120

NMR (CDCl₃) δppm: 2.20–2.90 (m,12H), 3.35 (s,3H), 3.90–4.30 (m,6H), 6.95–7.25 (m,9H), 7.66–7.82 (m,2H), 8.07 (d,1H,J=8.4), 8.83 (d,1H,J=8.91)

EXAMPLE 72

5-[3-(4-(Xanthene-9-yl)piperazin-1-yl)-2-hydroxypropoxy]quinoline

Following the same procedure as in Example 1-(b), reaction and treatment were carried out using the epoxy compound prepared in Example 1-(a) and N-(xanthene-9-yl)piperazine.

IR (KBr) νcm⁻¹: 3400, 2800, 1580, 1460, 1440, 1240, 980, 740

NMR δppm (CDCl₃): 2.3–2.7 (m,10H), 4.0–4.15 (m,3H), 4.83 (s,1H), 6.81 (d,1H), 7.1–7.4 (m,9H), 7.56 (t,1H), 7.67 (d,1H), 8.52 (d,1H), 8.88 (d,1H)

EXAMPLE 73

5-[3-(N-Methyl-3-(5-iminodibenzyl)propylamino)-2-hydroxypropoxy]quinoline

Following the same procedure as in Example 1-(b), reaction and treatment were carried out using an epoxy compound prepared in Example 1-(a) and desipramine in order to obtain the desired compound.

IR KBr νmax cm⁻¹ (HCl salt): 3380, 2640, 1630, 1590, 1485, 1470, 1410, 1380, 1280, 1110

NMR (CDCl₃) δppm: 1.65–1.76 (2H,m), 2.18 (3H,s), 2.37–2.58 (4H,m), 3.11 (4H,s), 3.67–3.86 (2H,m), 3.98–4.10 (3H,m), 6.74–6.86 (3H,m), 6.97–7.08 (6H,m), 7.27–7.32 (1H,m), 7.48–7.67 (2H,m), 8.42–8.50 (1H,m), 8.81–8.84 (1H,dd)

EXAMPLE 74

5-[3-(4-Diphenylmethylpiperazin-1-yl)-2-hydroxypropylthio]qunoline

In 10 ml of chloroform were dissolved 1.2 g of 4-(3-chloro-2-hydroxypropy)-1-diphenylmethylpiperazine prepared in Example 23-(b) and 220 mg of 5-mercaptoquinoline, and 311 mg of DBU was further added thereto. Afterward, the liquid was allowed to stand at room temperature for 12 days. The reaction liquid was poured into 20 ml of water and was then extracted twice with methylene chloride. The resultant organic layer was separated, then dried with an anhydrous Glauber's salt, and was distilled off under reduced pressure. The resultant residue was purified through a silica gel chromatograph (an AcOEt effluent solvent was used) in order to obtain 130 mg of the desired compound.

IR max νcm⁻¹ (KBr): 3300, 2520, 1620, 1580, 1420, 1390, 1360, 1290, 1070, 910

NMR δppm (CDCl₃): 2.3–2.7 (m,12H), 3.8–3.9 (m,1H), 4.21 (s,1H), 7.1–7.7 (m,13H), 8.00 (dd,1H), 8.75 (dd,1H), 8.94 (dd,1H)

EXAMPLE 75

5-[3-(4-(Dibenzosuberane-5-yl)piperazin-1-yl)-2-hydroxy-propylthio]quinoline

The same procedure as in Example 23-(b) was repeated with the exception that diphenylmethylpiperazine was replaced with 4-(dibenzosuberane-5-yl)piperazine, in order to prepare 4-(3-chloro-2-hydroxypropyl)-1-(dibenzosuberane5-yl)piperazine, and reaction and treatment were then carried out using 932 mg of the thus prepared piperazine compound and 270 mg of 5-mercaptoquinoline in accordance with the same procedure as in Example 74, so that 220 mg of the desired compound was obtained.

IR max νcm⁻¹ (KBr): 3300, 2500, 1580, 1390, 1360, 1300, 1070, 860, 760, 650, 620

NMR δppm (CDCl₃): 2.1–2.7 (m,12H), 2.7–2.9 (m,2H), 3.8–4.1 (m,4H), 7.0–7.8 (m,11H), 8.00 (d,1H), 8.75 (dd,1H), 8.93 (dd,1H)

EXAMPLE 76

5-[3-(4-(Dibenzosuberane-5-yl)piperazin-1-yl)-2-hydroxypropoxy]-2,4-bis(trifluoromethyl)quinoline (a) Following the same procedure as in Example 1-(a), reaction and treatment were carried out using 0.38 g of 2,4-bis(trifluoromethyl)-5-hydroxyquinoline, in order to obtain 0.18 g of 5-(2,3-epoxy)propoxy-2,4-bis(trifluoromethyl)quinoline.

NMR δppm (CDCl₃): 2.7–2.8 (m,1H), 2.9–3.0 (m,1H), 3.4–3.5 (m,1H), 4.1–4.4 (m,2H), 7.19 (d,1H), 7.81 (t,1H), 7.96 (d,1H), 8.08 (s,1H)

(b) Following the same procedure as in Example 1-(b), reaction and treatment were carried out using 0.18 g of the above synthesized epoxy compound and 0.16 g of (dibenzosuberane-5-yl)piperazine synthesized in Example 2-(a), in order to obtain 0.3 g of 5-[3-(4-(dibenzosuberane-5-yl)piperazin-1-yl)-2-hydroxypropoxy]-2,4-bis(trifluoromethyl)quinoline.

NMR δppm (CDCl₃): 2.16–2.90 (m,12H), 3.9–4.3 (m,6H), 7.0–7.3 (m,10H), 7.80 (t,1H), 7.94 (d,1H), 8.05 (s,1H)

EXAMPLE 77

5-[3-(4-(Dibenzosuberene-5-ylidene)piperidine-1-yl)2-hydroxypropoxy]quinoline

Following the same procedure as in Example 1-(b), reaction and treatment were carried out using 1.66 g of 4-(dibenzosuberene-5-ylidene)piperidine and 1.65 g of epoxy compound synthesized in Example 1-(a), in order to obtain 1.32 g of 5-[3-(4-(dibenzosuberene-5-ylidene)-piperidine-1-yl)-2-hydroxypropoxy]quinoline.

IR $\nu cm^{-1}$ (KBr): 3400, 2700, 1645, 1590, 1410

NMR $\delta$ppm (CDCl$_3$): 2.1–2.9 (m,10H), 3.9–4.2 (m,3H), 6.78 (d,1H), 6.86 (s,2H), 7.1–7.3 (m,8H), 7.50 (t,1H), 7.63 (d,1H), 8.47 (d,1H), 8.81 (d,1H)

EXAMPLE 78

5-[2-Hyroxy-3-(4-(5-hydroxydibenzosuberane-5-yl)piperidine-1-yl)propoxy]quinoline Following the same procedure as in Example 1-(b), reaction and treatment were carried out using 0.78 g of 4-(5-hydroxydibenzosuberane-5-yl)piperidine and 0.80 g of epoxy compound synthesized in Example 1-(a), in order to obtain 0.99 g of 5-[2-hydroxy-3-(4-(5-hydroxydibenzosuberane-5-yl)piperidine-1-yl)propoxy]quinoline.

IR $\nu cm^{-1}$ (KBr): 3400, 2700, 1630, 1590, 1410, 1280, 1105, 790

NMR $\delta$ppm (CDCl$_3$): 1.2–2.6 (m, 12H), 2.9–3.05 (m,2H), 3.43–3.52 (m,2H), 4.0–4.1 (m,1H), 4.15 (d,2H), 6.82 (d,1H), 7.0–7.2 (m,6H), 7.33 (dd,1H), 7.55 (t,1H), 7.65 (d,1H), 7.80 (d,2H), 8.51 (d,1H), 8.86 (dd,1H)

EXAMPLE 79

5-[2-Hydroxy-3-(4-(5-hydroxydibenzosuberene-5-yl)piperidine-1-yl)propoxy]quinoline Following the same procedure as in Example 1-(b), reaction and treatment were carried out using 1.60 g of 4-(5-hydroxydibenzosuberene-5-yl)piperidine and 1.08 g of epxoy compound synthesized in Example 1-(a), in order to obtain 1.41 g of 5-[2-hydroxy-3-(4-(5-hydroxydibenzosuberene-5-yl)piperidine-1-yl)propoxy]quinoline.

IR $\nu cm^{-1}$ (KBr): 3350, 2700, 1630, 1590, 1410, 1280, 1105, 790

NMR $\delta$ppm (CDCl$_3$): 1.4 (t,2H), 1.7 (t,1H), 2.0 (t,1H), 2.4–3.0 (m,8H), 4.0–4.2 (m,3H), 6.79 (d,1H), 6.92 (s,2H), 7.1–7.4 (m,7H), 7.52 (t,1H), 7.65 (dd,1H), 7.89 (dd,2H), 8.45 (dd,1H), 8.83 (dd,1H)

EXAMPLE 80

5-[3-(4-(Dibenzosuberane-5-ylidene)piperidine-1-yl)-2-hydroxypropoxy]quinoline

Following the same procedure as in Example 1-(b), reaction and treatment were carried out using 0.41 g of 4-(dibenzosuberane-5-yliene)piperidine and 0.40 g of epoxy compound synthesized in Example 3-(a), in order to obtain 0.4 g of 5-[3-(4-(dibenzosuberane-5-ylidene)-piperidine-1-yl)-2-hydroxypropoxy]quinoline.

IR $\nu cm^{-1}$ (KBr): 3400, 2920, 1630, 1590, 1410, 1280, 1100, 790

NMR $\delta$ppm (CDCl$_3$): 2.3–3.0 (m,12H), 3.3–3.5 (m,2H), 4.0–4.3 (m,3H), 6.82 (d,1H), 6.9–7.2 (m,8H), 7.32 (dd,1H), 7.54 (t,1H), 7.66 (d,1H), 8.52 (dd,1H), 8.85 (dd,1H)

EXAMPLE 81

5-[3-(4-(Dibenzosuberane-5-yl)piperidine-1-yl)-2-hydroxypropoxy]quinoline

Following the same procedure as in Example 1-(b), reaction and treatment were carried out using 1.60 g of 4-(dibenzosuberane-5-yl)piperidine and 1.45 g of epoxy compound synthesized in Example 1-(a), in order to obtain 0.97 g of 5-[3-(4-(dibenzosuberane-5-yl)piperidine-1-yl)-2-hydroxypropoxy]quinoline.

IR $\nu cm^{-1}$ (KBr): 3400, 2700, 1630, 1590, 1410, 1280, 1105, 790

NMR $\delta$ppm (CDCl$_3$): 2.1–3.0 (m,12H), 3.3–3.5 (m,2H), 4.0–4.3 (m,3H), 6.83 (d,1H), 7.0–7.1 (m,8H), 7.33 (dd,1H), 7.54 (t,1H), 7.66 (d,1H), 8.52 (d,1H), 8.86 (dd,1H)

EXAMPLE 82

5-[3-(N-Methyl-N-(3-(5H-10,11-dihydrodibenzo(b,f)-azepin-5-yl)propyl)amino]-2-hydroxypropoxy]quinoline Following the same procedure as in Example 1-(b), reaction and treatment were carried out using 1.0 g of H-10,11-dihydro-5-[3-(methylamino)propyl]-dibenzo[b,f]azepine and 0.67 g of epoxy compound synthesized in Example 1-(a), in order to obtain 1.07 g of 5-[3-(N-methyl-N-(3-(5H-10,11-dihydrodibenzo[b,f]azepin-5-yl)propyl)amino]-2-hydroxypropoxy]quinoline.

IR $\nu cm^{-1}$ (KBr): 3380, 2660, 1630, 1590, 1485, 1410, 1280, 1110

NMR $\delta$ppm (CDCl$_3$): 1.7 (m,2H), 2.20 (s,3H), 2.35–2.61 (m,4H), 3.10 (s,4H), 3.65–3.80 (m,2H), 3.95–4.15 (m,3H), 4.20–4.35 (m,1H), 6.7–6.9 (m,3H), 6.95–7.15 (m,6H), 7.3 (m,1H), 7.45–7.70 (m,2H), 8.45 (m,1H), 8.85 (m,1H)

EXAMPLE 83

5-[3-(4-(Dibenzosuberane-5-yl)piperazine-1-yl)propoxy]quinoline

Following the same procedure as in Example 1-(b), reaction and treatment were carried out using 0.63 g of 4-(dibenzosuberane-5-yl)piperazine and 0.6 g of quinoline compound synthesized in Example 32-(a), in order to obtain 0.7 g of 5-[3-(4-(dibenzosuberane-5-yl)piperazine-1-yl)propoxy]quinoline.

IR $\nu cm^{-1}$ (KBr): 3420, 1640, 1600, 1420, 1380, 1285, 1110

NMR $\delta$ppm (CDCl$_3$): 2.0–2.95 (m,14H), 3.8–4.1 (m,3H), 4.13–4.25 (m,2H), 6.83 (d,1H), 7.0–7.2 (m,8H), 7.35 (m,1H), 7.51–7.7 (m,2H), 8.85 (dd,1H), 8.9 (dd,1H)

EXAMPLE 84

5-[3-(4-(Diphenylmethylene)piperidine-1-yl)propoxy]-quinoline

Following the same procedure as in Example 1-(b), reaction and treatment were carried out using 0.68 g of 4-(diphenylmethylene)piperidine and 0.55 g of quinoline compound synthesized in Example 32-(a), in order to obtain 0.59 g of 5-[3-(4-(diphenylmethylene)piperidine-1-yl)propoxy]quinoline.

IR $\nu cm^{-1}$ (KBr): 3400, 2920, 1630, 1590, 1460, 1410, 1375, 1280

NMR $\delta$ppm (CDCl$_3$): 2.1–2.7 (m, 12H), 4.27 (t,2H), 6.85 (d,1H), 7.1–7.4 (m,11H), 7.56–7.7 (m,2H), 8.59 (dd,1H), 8.9 (dd,1H)

EXPERIMENTAL EXAMPLE 1

Potentiating Effect of the Compounds on Incorporation of Anticancer Drugs into Drug-resistant Cancer Cells Adriamycin resistant strain 2780 AD cells of human ovarian cancer A2780 cells (A. M. Rogan et al., Science 224, 994–996, 1984) were suspended at a concentration of $1 \times 10^6$/ml in RPMI-1640 medium supplemented with 5% fetal calf serum, and 1 ml of the cancer cell suspension was dispensed into each well of a multi-well culture plate (24 wells, 16 cm in diameter) and then incubated at 37° C. in an atmosphere of 5% $CO_2$. After 24 hours incubation, the medium in each well was replaced by 0.5 ml of RPMI-1640 medium supplemented containing 20 nM $^3$H-vincristine ($1 \times 10^4$ dpm/pmol), 5% fetal calf serum and 10 mM Hepes buffer. Five microliters of a solution of the compound to be tested, which had been dissolved in DMSO and diluted with serine-phosphate buffer (at a concentration of 1.0 microgram/ml or 10.0 micrograms/ml), was added to each well and the incubation was continued at 37° C. in 5% $CO_2$ for 2 hours. The resultant cells were washed in cold saline-phosphate buffer. In each well was added 0.5 ml of 0.2N NaOH, and the resulting cell suspension in each well was independently transferred into a vial and then heated in a water bath at 56° C. for 30–60 minutes to dissolve the cells. After adding 4 ml of acid aquazole 2, the amount of $^3$H-vincristine incorporated into the cells was determined by a fluid scintillation counter.

The potentiating effect was expressed by percentage (%) of the amount of vincristine incorporated into the cells treated with the test compound compared to that incorporated into the control cells without treatment. The results are shown in Table 1.

EXPERIMENTAL EXAMPLE 2

Potentiating Effect of the Compounds on Activity of Anticancer Drugs

Adriamycin resistant strain K562/ADM cells of human myeloleukemia K562 cells were suspended at a concentration of $2 \times 10^4$/ml in RPMI-1640 medium supplemented with 5% fetal calf serum, and 2 ml of the cancer cell suspension was dispensed into each tube ($12 \times 75$ mm) and then incubated at 37° C. in 5% $CO_2$. After 6 hours incubation, vincristine (0–3,000 ng/ml) and the test compound (0.3, 1 or 3 ng/ml) were added, and the incubation was continued at 37° C. in 5% $CO_2$ for 2 hours. The cell suspension was added to 9.5 ml of ISTON II, and the number of cells were counted by a Coulter counter to estimate the vincristine concentration at which 50% growth was inhibited, $IC_{50}$ (ng/ml).

Two cases from the results of the experiments, $IC_{50}$ value and potentiating effect, with the compounds given in Table 1 as set forth are given in Table 2. Likewise, the potentiating effect on the activity of drugs was observed with the other compounds in Table 1 (data omitted).

EXPERIMENTAL EXAMPLE 3

Potentiating Effect on the Activity of Anticancer-Drugs on Mice having Vincristine-resistant Mouse Leukemia Vincristine-resistant strain P388/VCR cells of mouse leukemia P388 cells ($1 \times 10^6$) were peritoneally transplanted into female CDFI mice, and then vincristine and the test compound given in Table 1 in combination were peritoneally administered once a day for 5 days.

Survival of animals was observed, and percentage (%) of surviving days of the animals administered with the test compound to those of the control animals, (T/C), were calculated. The results are partially shown in Tables 3(a)–3(f).

A similar effect on survival was observed with the other compounds in Table 1 (data omitted).

TABLE 1

| Compound (Example #) | $^3$H-vincristine accumulation (%) Concentration of compound (μg/ml) | |
|---|---|---|
| | 1 | 10 |
| None (Control) | 100 | 100 |
| 1 | 717 | 747 |
| 2 | 663 | 709 |
| 3 | 731 | 774 |
| 4 | 438 | 770 |
| 5 | 732 | 1040 |
| 6 | 1035 | 1135 |
| 7 | 972 | 1040 |
| 8 | 394 | 863 |
| 9 | 721 | 947 |
| 10 | 642 | 932 |
| 11 | 735 | 1073 |
| 12 | 568 | 831 |
| 13 | 517 | 805 |
| 14 | 119 | 871 |
| 15 | 840 | 1072 |
| 16 | 850 | 982 |
| 17 | 730 | 1040 |
| 18 | 743 | 761 |
| 19 | 374 | 524 |
| 20 | 794 | 1054 |
| 21 | 727 | 745 |
| 22 | 723 | 743 |
| 23 | 723 | 1604 |
| 24 | 146 | 931 |
| 25 | 858 | 1376 |
| 26 | 177 | 1111 |
| 27 | 1146 | 1239 |
| 28 | 1705 | 1147 |
| 29 | 246 | 1161 |
| 30 | 597 | 1083 |
| 31 | 428 | 799 |
| 32 | 816 | 1413 |
| 33 | 447 | 1081 |
| 34 | 785 | 1034 |
| 35 | 654 | 627 |
| 36 | 821 | 716 |
| 37 | 549 | 1000 |
| 38 | 378 | 819 |
| 39 | 236 | 908 |
| 40 | 259 | 1017 |
| 41 | 584 | 1231 |
| None (control) | 100 | 100 |
| 42 | 624 | 1011 |
| 43 | 531 | 1297 |
| 44 | 636 | 934 |
| 45 | 307 | 982 |
| 46 | 142 | 987 |
| 47 | 322 | 879 |
| 48 | 215 | 798 |
| 49 | 213 | 612 |
| 50 | 559 | 668 |
| 51 | 534 | 798 |
| 52 | 379 | 910 |
| 53 | 658 | 794 |
| 54 | 253 | 777 |
| 55 | 452 | 756 |
| 56 | 321 | 735 |
| 57 | 572 | 732 |
| 58 | 619 | 843 |
| 59 | 561 | 685 |
| 60 | 643 | 760 |
| 61 | 519 | 602 |
| 62 | 525 | 1125 |
| 63 | 773 | 1130 |

TABLE 1-continued

| Compound (Example #) | $^3$H-vincristine accumulation (%) Concentration of compound (μg/ml) | |
|---|---|---|
| | 1 | 10 |
| 64 | 425 | 900 |
| 65 | 297 | 985 |
| 66 | 488 | 1071 |
| 67 | 730 | 1065 |
| 68 | 671 | 1097 |
| 69 | 738 | 941 |
| 70 | 252 | 960 |
| 71 | 501 | 921 |
| 72 | 112 | 144 |
| 74 | 626 | 1024 |
| 75 | 587 | 1064 |
| 76 | 130 | 304 |
| 77 | 1019 | 1192 |
| 78 | 943 | 1077 |
| 79 | 841 | 963 |
| 80 | 942 | 1143 |
| 81 | 992 | 1232 |
| 82 | 667 | 1273 |
| 83 | 957 | 1263 |
| 84 | 159 | 878 |

TABLE 2

| Compound (Example #) | $IC_{50}$ (ng/ml)[1] Concentration of compound (μg/ml) | | | |
|---|---|---|---|---|
| | 0 | 0.3 | 1 | 3 |
| 1 | 655 | 4.3(151.2)[2] | 1.9(342.1) | 1.5(433.3) |
| 2 | 655 | 2.0(330.3) | 1.7(388.0) | 1.2(550.0) |

[1]Vincristine concentration at which 50% of the growth of adriamycin-resistant human myeloleukemia K562 cells (K562/ADM) was inhibited.
[2]Values in parentheses, which indicate effect in potentiating vincristine activity by test compounds, are multiples of the control. The calculation was made by dividing the value of $IC_{50}$ for the individual test compound by that for the control (without test compound), 655.

TABLE 3-(a)

| Compound Example # | Concentration (mg/kg) | Vincristine (ug/kg) | Average surviving period (days) | T/C* (%) |
|---|---|---|---|---|
| Control | (none) | 0 | 11.2 ± 1.0 | 100 |
| None | (none) | 100 | 11.5 ± 0.5 | 103 |
| 1 | 3 | 100 | 12.4 ± 0.2 | 111 |
| 1 | 10 | 100 | 12.2 ± 0.4 | 109 |
| 1 | 30 | 100 | 12.8 ± 0.4 | 114 |
| 2 | 3 | 100 | 12.6 ± 0.2 | 113 |
| 2 | 30 | 100 | 15.2 ± 0.7 | 136 |
| 44 | 10 | 100 | 12.5 ± 0.0 | 112 |
| 44 | 30 | 100 | 13.8 ± 1.0 | 123 |

*Rate of life prolongation

TABLE 3-(b)

| Compound Example # | Concentration (mg/kg) | Vincristine (ug/kg) | Average surviving period (days) | T/C* (%) |
|---|---|---|---|---|
| Control | (none) | 0 | 10.5 ± 0.6 | 100 |
| None | (none) | 100 | 11.5 ± 0.4 | 110 |
| 6 | 30 | 100 | 13.4 ± 0.7 | 128 |
| 7 | 30 | 100 | 12.9 ± 0.5 | 123 |
| 11 | 30 | 100 | 12.1 ± 0.5 | 115 |
| 15 | 30 | 100 | 12.3 ± 0.4 | 117 |
| 16 | 30 | 100 | 13.9 ± 1.4 | 132 |
| 18 | 30 | 100 | 13.8 ± 0.4 | 131 |
| 22 | 30 | 100 | 13.9 ± 0.4 | 132 |

*Rate of life prolongation

TABLE 3-(c)

| Compound Example # | Concentration (mg/kg) | Vincristine (ug/kg) | Average surviving period (days) | T/C* (%) |
|---|---|---|---|---|
| Control | (none) | 0 | 10.3 ± 0.7 | 100 |
| None | (none) | 100 | 10.8 ± 0.8 | 105 |
| 27 | 30 | 100 | 12.3 ± 0.3 | 119 |
| 5 | 30 | 100 | 12.8 ± 0.8 | 124 |
| 32 | 30 | 100 | 11.3 ± 0.4 | 110 |
| 17 | 30 | 100 | 11.8 ± 1.1 | 115 |
| 35 | 30 | 100 | 11.9 ± 0.7 | 116 |
| 36 | 30 | 100 | 12.6 ± 0.9 | 122 |
| 20 | 30 | 100 | 13.7 ± 1.0 | 133 |
| 21 | 30 | 100 | 12.5 ± 0.6 | 121 |

*Rate of life prolongation

TABLE 3-(d)

| Compound Example # | Concentration (mg/kg) | Vincristine (ug/kg) | Average surviving period (days) | T/C* (%) |
|---|---|---|---|---|
| Control | (none) | 0 | 11.0 ± 0.4 | 100 |
| None | (none) | 100 | 10.7 ± 0.4 | 97 |
| 3 | 30 | 100 | 11.0 ± 0.6 | 100 |
| 4 | 30 | 100 | 11.8 ± 0.4 | 107 |
| 41 | 30 | 100 | 13.2 ± 1.8 | 120 |
| 42 | 30 | 100 | 13.9 ± 2.4 | 126 |
| 10 | 30 | 100 | 12.3 ± 1.4 | 112 |
| 12 | 30 | 100 | 12.5 ± 0.5 | 114 |
| 13 | 30 | 100 | 15.3 ± 0.5 | 139 |
| 34 | 30 | 100 | 10.8 ± 0.8 | 98 |

*Rate of life prolongation

TABLE 3-(e)

| Compound Example # | Concentration (mg/kg) | Vincristine (ug/kg) | Average surviving period (days) | T/C* (%) |
|---|---|---|---|---|
| Control | (none) | 0 | 10.6 ± 0.4 | 100 |
| None | (none) | 100 | 11.3 ± 0.5 | 107 |
| 8 | 30 | 100 | 12.2 ± 0.6 | 115 |
| 9 | 30 | 100 | 14.2 ± 0.6 | 134 |
| 53 | 30 | 100 | 11.8 ± 0.8 | 111 |
| 55 | 30 | 100 | 12.7 ± 0.3 | 120 |
| 57 | 30 | 100 | 13.1 ± 0.4 | 124 |
| 58 | 30 | 100 | 13.8 ± 1.8 | 130 |
| 59 | 30 | 100 | 13.2 ± 1.2 | 125 |
| 60 | 30 | 100 | 12.4 ± 0.7 | 117 |
| 61 | 30 | 100 | 11.5 ± 0.3 | 108 |

*Rate of life prolongation

TABLE 3-(f)

| Compound Example # | Concentration (mg/kg) | Vincristine (ug/kg) | Average surviving period (days) | T/C* (%) |
|---|---|---|---|---|
| Control | (none) | 0 | 10.7 ± 1.0 | 100 |
| None | (none) | 100 | 11.3 ± 0.6 | 106 |
| 77 | 30 | 100 | 13.8 ± 1.2 | 129 |
| 78 | 30 | 100 | 12.8 ± 0.8 | 120 |
| 80 | 30 | 100 | 14.3 ± 0.6 | 134 |
| 81 | 30 | 100 | 13.2 ± 0.9 | 123 |
| 82 | 30 | 100 | 11.2 ± 1.4 | 105 |
| 83 | 30 | 100 | 13.5 ± 0.5 | 126 |
| 84 | 30 | 100 | 13.0 ± 0.7 | 121 |

*Rate of life prolongation

Although the invention has been described with reference to preferred embodiments, it is to be understood that variations and modifications will be apparent to those skilled in the art and are included within the invention. Such variations and modifications are to be considered within the purview and the scope of the claims appended hereto.

What is claimed is:

1. A compound of the formula:

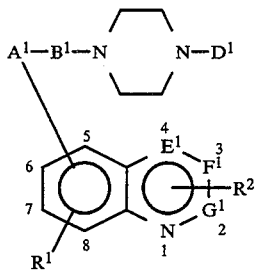 (I)

in which $A^1$ represents an oxygen or sulfur atom, an amino or $-NR^3$ group, which is bound to any of positions 5 to 8 on the condensed ring; $B^1$ represents $-(CH_2)_n-$ or

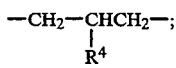

$D^1$ represents

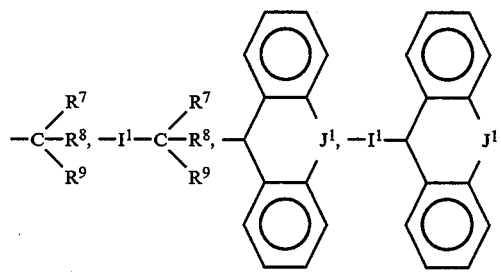

$E_1$, $F_1$ and $G^1$ each independently represent a carbon or nitrogen atom; $R^1$ and $R^2$ each independently represent a hydrogen or halogen atom, a lower alkyl, amino group, substituted amino group, a lower alkoxy, lower alkylthio, lower alkylsulfonyl, trifluoromethyl, cyano, nitro or andde, where $R^1$ and $R^2$ may be on any position available on the condensed ring or one each on each of the rings or both on the same ring of which the condensed ring is formed; $R^3$ represents a lower alkyl or acyl group; $R^4$ represents a hydroxyl or lower acyloxy group; $R^7$ is a hydrogen atom and $R^8$ and $R^9$ each independently represent a phenyl, halogenophenyl, alkylphenyl, alkoxyphenyl, aminophenyl, alkylaminophenyl, acylaminophenyl or hydroxyphenyl group; $I^1$ represents an oxygen atom or

;

$J^1$ represents $-(CH_2)_n-$, $-CH=CH-$, $-OCH_2-$ or an oxygen atom; n represents an integer of 2 to 5; and m represents an integer 0, 1 or 2, or a pharmaceutically acceptable salt thereof.

2. A compound as set forth in claim 1, wherein formula (I) represents

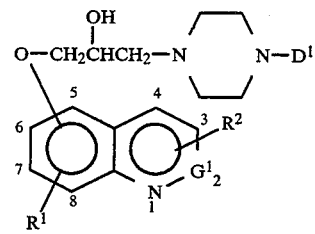 (II)

in which

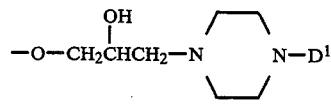

is at any of positions 5 to 8 on the condensed ring and $D^1$, $G^1$, $R^1$ and $R^2$ are the same as those of formula I, or a pharmaceutically acceptable salt thereof.

3. The compound of claim 2 wherein, in formula II, $G^1$ represents a carbon atom, $R^1$ and $R^2$ each independently represent a hydrogen or halogen atom or a lower alkyl group, $R^7$, $R^8$ and $R^9$ are the same as those of formula II;

$J^1$ represents $-(CH_2)_2-$ or $C=CH-$; and $I^1$ represents

or a pharmaceutically acceptable salt thereof.

4. The compound of claim 2 wherein, in formula II, is at the 5 position of the condensed ring.

5. A compound as set forth in claim 1 wherein $D^1$ represents

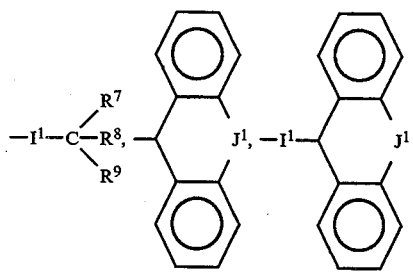

and $I^1$, $J^1$, $R^7$, $R^8$, $R^9$ are the same as claim 1.

6. A compound as set, forth in claim 5 wherein $A^1$ represents an oxygen atom, $B^1$ represents a

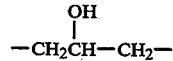

group, or a pharmaceutically acceptable salt thereof.

7. A compound as set forth in claim 6 wherein

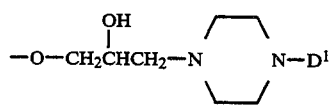

group is at the 5-position of condensed ring.

8. The compound as set forth in claim 2, wherein the compound of formula II is 5-[3-[4-(dibenzosuberan-5-yl)piperazin-1-yl]-2-hydroxypropoxy]quinoline or a pharmaceutically acceptable salt, thereof.

9. The compound as set forth in claim 2 wherein the compound of formula II is 5-[3-[4-(dibcnzosuberan-5-ylidene)piperazin-1-yl]-2-hydroxypropoxy]quinoline or a pharmaceutically acceptable salt thereof.

10. The compound as set forth in claim 2, wherein the compound of formula II is 5-[3-[4-(2,2-diphenylacetyl)-piperazin-1-yl]-2-hydroxypropoxy]quinoline or a pharmaceutically acceptable salt thereof.

11. A pharmaceutical composition for potentiating the effect of anticancer drugs, which comprises a compound of formula (I) as set forth in claim 1 or 5 together with a pharmaceutically acceptable carrier or diluent.

12. The pharmaceutical composition as set forth in claim 11 also containing a non-metabolic anticancer agent.

13. The pharmaceutical composition as set forth in claim 12 in which the non-antimetabolic agent is vincristine or adriomycin.

14. The pharmaceutical composition of claim 11 is a peroral preparation in a form of tablet, grantfie, powder, suspension, capstile, syrup, injection, depository or isotonic fluid for infusion.

15. A method of treating cancer, which comprises potentiating the effect of an anticancer drug by administering to a patient in need of same an effective amount of an anticancer drug and the compound of formula (I) as set forth in claim 1 or 5.

16. The method as set forth in claim 15 in which the amount of the compound administered is in the range 1 to 1,000 mg a day in a single dose or divided doses.

17. A method as claimed in claim 15 wherein the compound of formula (I) is 5-[3-[4-(2,2-diphenylacetyl)piperazin-1-yl]-2-hydroxypropoxy]quinoline or a pharmaceutically acceptable salt thereof.

* * * * *

Disclaimer 5,405,843—Nobuyuki Fukazawa; Makoto Odate; Tsuneji Suzuki, all of Yokohama; Kengo Otsuka, Kamakura; Takashi Tsuruo; Wakao Sato, both of Tokyo, all of Japan. QUINOLINE DERIVATIVES. Patent dated Apr. 11, 1995. Disclaimer filed September 10, 2003, by the assignee, Schering Aktiengesellschaft Corporation.

The term of this patent shall not extend beyond the expiration date of Pat. No. 5,112,817.

*(Official Gazette, November 11, 2003)*